(12) United States Patent
Gunning et al.

(10) Patent No.: US 6,919,180 B2
(45) Date of Patent: Jul. 19, 2005

(54) HYBRIDIZATION RATE ENHANCEMENT FOR SUBSTRATE-BOUND SPECIFIC NUCLEIC ACID-BINDING AGENTS

(75) Inventors: Kerry B. Gunning, Houston, TX (US); Tom Powdrill, The Woodlands, TX (US); Michael Hogan, Tucson, AZ (US)

(73) Assignee: Sigma Genosys, L.P., The Woodlands, TX (US)

( * ) Notice: Subject to any disclaimer, the term of this patent is extended or adjusted under 35 U.S.C. 154(b) by 303 days.

(21) Appl. No.: 10/104,307

(22) Filed: Mar. 22, 2002

(65) Prior Publication Data

US 2003/0180729 A1 Sep. 25, 2003

(Under 37 CFR 1.47)

(51) Int. Cl.[7] .......................... C12Q 1/68; G01N 33/53
(52) U.S. Cl. ........................................... 435/6; 435/7.1
(58) Field of Search ................... 435/6, 7.1; 436/94

(56) References Cited

U.S. PATENT DOCUMENTS

| | | | | |
|---|---|---|---|---|
| 5,132,207 A | * | 7/1992 | Kohne et al. ................... | 435/6 |
| 5,512,436 A | * | 4/1996 | Stone ............................ | 435/6 |
| 6,264,825 B1 | * | 7/2001 | Blackburn et al. ........ | 205/777.5 |
| 6,331,274 B1 | | 12/2001 | Ackley et al. | |
| 2002/0164614 A1 | * | 11/2002 | Becker .......................... | 435/6 |

OTHER PUBLICATIONS

Belosludtsev, Y., et al., "Nearly Instantaneous, Cation–Independent, High Selectivity Nucleic Acid Hybridization to DNA Microarrays", Biochem Biophys Rsch Comm, 2001, vol. 282(5), pp. 1263–1267.

Zhang, P., et al., "Acceleration of Nucleic Acid Hybridization on DNA Microarrays Driven by pH Tunable Modifications", Nucleosides, Nucleotides & Nucleic Acids, 2001, vol. 282(4–7), pp. 1251–1254.

\* cited by examiner

*Primary Examiner*—Kenneth R. Horlick
(74) *Attorney, Agent, or Firm*—Senniger Powers

(57) ABSTRACT

The invention relates to kits and methods for hybridizing nucleic acids with a specific nucleic acid-binding agent, such as a complementary nucleic acid. Previously, others have hybridized a nucleic acid with such an agent bound to a substrate. The improved methods described herein comprise binding a polycationizable attractor compound to the substrate, in addition to the agent. Examples of suitable polycationizable attractor compounds include polypeptides, including those with tunable cationizable amino acid residues, such as histidine. Compositions, kits, devices, and methods that make use of this hybridization rate enhancement technology are disclosed.

55 Claims, 8 Drawing Sheets

| P0 | |
|---|---|
| P1 | P2 |
| P3 | P4 |
| P5 | P6 |
| P7 | P8 |
| P9 | P10 |
| P11 | P12 |
| P13 | P14 |

| P11 | P10 | P21 | P22 |
| P13 | P12 | P14 | P23 |
| P24 | P15 | P17 | P18 |
| P20 |     |     |     |

P20    P17    P18

Co-Print Ratio

1 : 0

1 :1.5

1 : 1

1 : 2

Co-Print Ratio

1 : 0

1 :1.5

1 : 1

1 : 2

SEQUENCE LISTING

```
<160> NUMBER OF SEQ ID NOS: 36
<210> SEQ ID NO 1
<211> LENGTH: 3
<212> TYPE: PRT
<213> ORGANISM: Artificial Sequence
<220> FEATURE:
<221> NAME/KEY: peptide
<222> LOCATION: (1)..(3)
<223> OTHER INFORMATION: synthetic peptide

<400> SEQUENCE: 1

His His Glu
1

<210> SEQ ID NO 2
<211> LENGTH: 4
<212> TYPE: PRT
<213> ORGANISM: Artificial Sequence
<220> FEATURE:
<221> NAME/KEY: peptide
<222> LOCATION: (1)..(4)
<223> OTHER INFORMATION: synthetic peptide

<400> SEQUENCE: 2
```

His His Phe Glu
1

<210> SEQ ID NO 3
<211> LENGTH: 3
<212> TYPE: PRT
<213> ORGANISM: Artificial Sequence
<220> FEATURE:
<221> NAME/KEY: peptide
<222> LOCATION: (1)..(3)
<223> OTHER INFORMATION: synthetic peptide

<400> SEQUENCE: 3

His Phe Gly
1

<210> SEQ ID NO 4
<211> LENGTH: 4
<212> TYPE: PRT
<213> ORGANISM: Artificial Sequence
<220> FEATURE:
<221> NAME/KEY: peptide
<222> LOCATION: (1)..(4)
<223> OTHER INFORMATION: synthetic peptide

<400> SEQUENCE: 4

His Phe Glu Gly
1

<210> SEQ ID NO 5
<211> LENGTH: 2
<212> TYPE: PRT
<213> ORGANISM: Artificial Sequence
<220> FEATURE:
<221> NAME/KEY: peptide
<222> LOCATION: (1)..(2)
<223> OTHER INFORMATION: synthetic peptide
<221> NAME/KEY: MOD_RES
<222> LOCATION: (2)..(2)
<223> OTHER INFORMATION: carboxyl terminal amide cap

<400> SEQUENCE: 5

His Glu
1

<210> SEQ ID NO 6
<211> LENGTH: 4
<212> TYPE: PRT
<213> ORGANISM: Artificial Sequence
<220> FEATURE:
<221> NAME/KEY: peptide
<222> LOCATION: (1)..(4)
<223> OTHER INFORMATION: synthetic peptide
<221> NAME/KEY: MOD_RES
<222> LOCATION: (4)..(4)
<223> OTHER INFORMATION: carboxyl terminal amide cap

<400> SEQUENCE: 6

His Phe Glu Asn
1

<210> SEQ ID NO 7
<211> LENGTH: 1
<212> TYPE: PRT
<213> ORGANISM: Artificial Sequence
<220> FEATURE:
<221> NAME/KEY: peptide
<222> LOCATION: (1)..(1)
<223> OTHER INFORMATION: synthetic peptide

```
<221> NAME/KEY: MOD_RES
<222> LOCATION: (1)..(1)
<223> OTHER INFORMATION: amine modified histidine

<400> SEQUENCE: 7

His
1

<210> SEQ ID NO 8
<211> LENGTH: 1
<212> TYPE: PRT
<213> ORGANISM: Artificial Sequence
<220> FEATURE:
<221> NAME/KEY: peptide
<222> LOCATION: (1)..(1)
<223> OTHER INFORMATION: synthetic peptide

<400> SEQUENCE: 8

His
1

<210> SEQ ID NO 9
<211> LENGTH: 3
<212> TYPE: PRT
<213> ORGANISM: Artificial Sequence
<220> FEATURE:
<221> NAME/KEY: peptide
<222> LOCATION: (1)..(3)
<223> OTHER INFORMATION: synthetic peptide

<400> SEQUENCE: 9

Gly Lys His
1

<210> SEQ ID NO 10
<211> LENGTH: 2
<212> TYPE: PRT
<213> ORGANISM: Artificial Sequence
<220> FEATURE:
<221> NAME/KEY: peptide
<222> LOCATION: (1)..(2)
<223> OTHER INFORMATION: synthetic peptide
<221> NAME/KEY: MOD_RES
<222> LOCATION: (2)..(2)
<223> OTHER INFORMATION: carboxyl terminal amide cap

<400> SEQUENCE: 10

Lys His
1

<210> SEQ ID NO 11
<211> LENGTH: 2
<212> TYPE: PRT
<213> ORGANISM: Artificial Sequence
<220> FEATURE:
<221> NAME/KEY: peptide
<222> LOCATION: (1)..(2)
<223> OTHER INFORMATION: synthetic peptide

<400> SEQUENCE: 11

Lys His
1

<210> SEQ ID NO 12
<211> LENGTH: 3
<212> TYPE: PRT
<213> ORGANISM: Artificial Sequence
<220> FEATURE:
<221> NAME/KEY: peptide
```

```
<222> LOCATION: (1)..(2)
<223> OTHER INFORMATION: synthetic peptide
<221> NAME/KEY: MOD_RES
<222> LOCATION: (2)..(2)
<223> OTHER INFORMATION: carboxyl terminal amide cap

<400> SEQUENCE: 12

Lys His His
1

<210> SEQ ID NO 13
<211> LENGTH: 3
<212> TYPE: PRT
<213> ORGANISM: Artificial Sequence
<220> FEATURE:
<221> NAME/KEY: peptide
<222> LOCATION: (1)..(3)
<223> OTHER INFORMATION: synthetic peptide

<400> SEQUENCE: 13

Lys His His
1

<210> SEQ ID NO 14
<211> LENGTH: 4
<212> TYPE: PRT
<213> ORGANISM: Artificial Sequence
<220> FEATURE:
<221> NAME/KEY: peptide
<222> LOCATION: (1)..(4)
<223> OTHER INFORMATION: synthetic peptide

<400> SEQUENCE: 14

Lys His His His
1

<210> SEQ ID NO 15
<211> LENGTH: 6
<212> TYPE: PRT
<213> ORGANISM: Artificial Sequence
<220> FEATURE:
<221> NAME/KEY: peptide
<222> LOCATION: (1)..(6)
<223> OTHER INFORMATION: synthetic peptide
<221> NAME/KEY: MOD_RES
<222> LOCATION: (6)..(6)
<223> OTHER INFORMATION: carboxyl terminal amide cap

<400> SEQUENCE: 15

Lys His His His His Lys
1               5

<210> SEQ ID NO 16
<211> LENGTH: 11
<212> TYPE: PRT
<213> ORGANISM: Artificial Sequence
<220> FEATURE:
<221> NAME/KEY: peptide
<222> LOCATION: (1)..(11)
<223> OTHER INFORMATION: synthetic peptide
<221> NAME/KEY: MOD_RES
<222> LOCATION: (11)..(11)
<223> OTHER INFORMATION: carboxyl terminal amide cap

<400> SEQUENCE: 16

Lys His His His His Lys His His His His Lys
1               5                   10

<210> SEQ ID NO 17
```

```
<211> LENGTH: 16
<212> TYPE: PRT
<213> ORGANISM: Artificial Sequence
<220> FEATURE:
<221> NAME/KEY: peptide
<222> LOCATION: (1)..(16)
<223> OTHER INFORMATION: synthetic peptide
<221> NAME/KEY: MOD_RES
<222> LOCATION: (16)..(16)
<223> OTHER INFORMATION: carboxyl terminal amide cap

<400> SEQUENCE: 17

Lys His His His His Lys His His His His Lys His His His His Lys
1               5                   10                  15

<210> SEQ ID NO 18
<211> LENGTH: 10
<212> TYPE: PRT
<213> ORGANISM: Artificial Sequence
<220> FEATURE:
<221> NAME/KEY: peptide
<222> LOCATION: (1)..(10)
<223> OTHER INFORMATION: synthetic peptide
<221> NAME/KEY: MOD_RES
<222> LOCATION: (10)..(10)
<223> OTHER INFORMATION: carboxyl terminal amide cap

<400> SEQUENCE: 18

Lys His Lys His Lys His Lys His Lys His
1               5                   10

<210> SEQ ID NO 19
<211> LENGTH: 3
<212> TYPE: PRT
<213> ORGANISM: Artificial Sequence
<220> FEATURE:
<221> NAME/KEY: peptide
<222> LOCATION: (1)..(3)
<223> OTHER INFORMATION: synthetic peptide

<400> SEQUENCE: 19

His Lys His
1

<210> SEQ ID NO 20
<211> LENGTH: 3
<212> TYPE: PRT
<213> ORGANISM: Artificial Sequence
<220> FEATURE:
<221> NAME/KEY: peptide
<222> LOCATION: (1)..(3)
<223> OTHER INFORMATION: synthetic peptide

<400> SEQUENCE: 20

His His Lys
1

<210> SEQ ID NO 21
<211> LENGTH: 4
<212> TYPE: PRT
<213> ORGANISM: Artificial Sequence
<220> FEATURE:
<221> NAME/KEY: peptide
<222> LOCATION: (1)..(4)
<223> OTHER INFORMATION: synthetic peptide
<221> NAME/KEY: MOD_RES
<222> LOCATION: (4)..(4)
<223> OTHER INFORMATION: carboxyl terminal amide cap

<400> SEQUENCE: 21
```

Lys His His His
1

<210> SEQ ID NO 22
<211> LENGTH: 5
<212> TYPE: PRT
<213> ORGANISM: Artificial Sequence
<220> FEATURE:
<221> NAME/KEY: peptide
<222> LOCATION: (1)..(5)
<223> OTHER INFORMATION: synthetic peptide
<221> NAME/KEY: MOD_RES
<222> LOCATION: (5)..(5)
<223> OTHER INFORMATION: carboxyl terminal amide cap

<400> SEQUENCE: 22

Lys His His His His
1               5

<210> SEQ ID NO 23
<211> LENGTH: 11
<212> TYPE: DNA
<213> ORGANISM: Artificial Sequence
<220> FEATURE:
<221> NAME/KEY: misc_feature
<222> LOCATION: (1)..(11)
<223> OTHER INFORMATION: synthetic oligonucleotide
<221> NAME/KEY: misc_feature
<222> LOCATION: (1)..(1)
<223> OTHER INFORMATION: 5' amine modification

<400> SEQUENCE: 23
gtagtgggcg t                                                        11

<210> SEQ ID NO 24
<211> LENGTH: 11
<212> TYPE: DNA
<213> ORGANISM: Artificial Sequence
<220> FEATURE:
<221> NAME/KEY: misc_feature
<222> LOCATION: (1)..(11)
<223> OTHER INFORMATION: synthetic oligonucleotide
<221> NAME/KEY: misc_feature
<222> LOCATION: (1)..(1)
<223> OTHER INFORMATION: 5' amine modification

<400> SEQUENCE: 24
gtagagggcg t                                                        11

<210> SEQ ID NO 25
<211> LENGTH: 13
<212> TYPE: DNA
<213> ORGANISM: Artificial Sequence
<220> FEATURE:
<221> NAME/KEY: misc_feature
<222> LOCATION: (1)..(13)
<223> OTHER INFORMATION: synthetic oligonucleotide
<221> NAME/KEY: misc_feature
<222> LOCATION: (1)..(1)
<223> OTHER INFORMATION: 5' amine modification

<400> SEQUENCE: 25
ctgtagtggg cgt                                                      13

<210> SEQ ID NO 26
<211> LENGTH: 13
<212> TYPE: DNA
<213> ORGANISM: Artificial Sequence
<220> FEATURE:
<221> NAME/KEY: misc_feature

```
<222> LOCATION: (1)..(13)
<223> OTHER INFORMATION: synthetic oligonucleotide
<221> NAME/KEY: misc_feature
<222> LOCATION: (1)..(1)
<223> OTHER INFORMATION: 5' amine modification

<400> SEQUENCE: 26
ctgtagaggg cgt                                                    13

<210> SEQ ID NO 27
<211> LENGTH: 15
<212> TYPE: DNA
<213> ORGANISM: Artificial Sequence
<220> FEATURE:
<221> NAME/KEY: misc_feature
<222> LOCATION: (1)..(15)
<223> OTHER INFORMATION: synthetic oligonucleotide
<221> NAME/KEY: misc_feature
<222> LOCATION: (1)..(1)
<223> OTHER INFORMATION: 5' amine modification

<400> SEQUENCE: 27
aactgtagtg ggcgt                                                  15

<210> SEQ ID NO 28
<211> LENGTH: 15
<212> TYPE: DNA
<213> ORGANISM: Artificial Sequence
<220> FEATURE:
<221> NAME/KEY: misc_feature
<222> LOCATION: (1)..(15)
<223> OTHER INFORMATION: synthetic oligonucleotide
<221> NAME/KEY: misc_feature
<222> LOCATION: (1)..(1)
<223> OTHER INFORMATION: 5' amine modification

<400> SEQUENCE: 28
aactgtagag ggcgt                                                  15

<210> SEQ ID NO 29
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: synthetic oligonucleotide
<221> NAME/KEY: misc_feature
<222> LOCATION: (1)..(1)
<223> OTHER INFORMATION: 5' amine modification

<400> SEQUENCE: 29
caactgtagt gggcgtcctg                                             20

<210> SEQ ID NO 30
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: synthetic oligonucleotide
<221> NAME/KEY: misc_feature
<222> LOCATION: (1)..(1)
<223> OTHER INFORMATION: 5' amine modification

<400> SEQUENCE: 30
caactgtaga gggcatcctg                                             20
```

```
<210> SEQ ID NO 31
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: synthetic oligonucleotide
<221> NAME/KEY: misc_feature
<222> LOCATION: (1)..(1)
<223> OTHER INFORMATION: 5' amine modification

<400> SEQUENCE: 31
caacagtaga gtgcatcctg                                                 20

<210> SEQ ID NO 32
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: synthetic oligonucleotide
<221> NAME/KEY: misc_feature
<222> LOCATION: (1)..(1)
<223> OTHER INFORMATION: 5' amine modification

<400> SEQUENCE: 32
cattgcaact gtagtgggcg tcctgctgtt                                      30

<210> SEQ ID NO 33
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: synthetic oligonucleotide
<221> NAME/KEY: misc_feature
<222> LOCATION: (1)..(1)
<223> OTHER INFORMATION: 5' amine modification

<400> SEQUENCE: 33
cattgcaaca gtagagggca tcctgctgtt                                      30

<210> SEQ ID NO 34
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: synthetic oligonucleotide
<221> NAME/KEY: misc_feature
<222> LOCATION: (1)..(1)
<223> OTHER INFORMATION: 5' amine modification

<400> SEQUENCE: 34
catttcaaca gtagagtgca tccttctgtt                                      30

<210> SEQ ID NO 35
<211> LENGTH: 15
<212> TYPE: DNA
<213> ORGANISM: Artificial Sequence
<220> FEATURE:
<221> NAME/KEY: misc_feature
<222> LOCATION: (1)..(15)
<223> OTHER INFORMATION: synthetic oligonucleotide
<221> NAME/KEY: misc_feature
<222> LOCATION: (15)..(15)
<223> OTHER INFORMATION: fluorescent label (Cy3)
```

```
-continued

<400> SEQUENCE: 35
acgcccacta cagtt                                                       15

<210> SEQ ID NO 36
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: synthetic oligonucleotide
<221> NAME/KEY: misc_feature
<222> LOCATION: (30)..(30)
<223> OTHER INFORMATION: fluorescent label (Cy3)

<400> SEQUENCE: 36
aacagcagga cgcccactac agttgcaatg                                       30
```

HYBRIDIZATION RATE ENHANCEMENT FOR SUBSTRATE-BOUND SPECIFIC NUCLEIC ACID-BINDING AGENTS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

Miniaturization of biological assays using microarray technology is essential for development of high-throughput screening (HTS). However, critical obstacles still remain before HTS is fully realized as a powerful and cost-effective research tool that is useful for developing fields such as pharmacogenetics. One of these obstacles is the rate at which nucleic acids hybridize with molecules in a microarray.

Enhancement of nucleic acid hybridization rates can help make HTS more valuable as a research tool by reducing time and resource requirements and increasing productivity. Currently, conventional hybridization times range from a few hours (e.g., in the case of single nucleotide polymorphism analysis) to overnight (12–18 hours; e.g., in the case of gene expression arrays). Thus, hybridization times for expression profiling microarrays are virtually the same as those required for Southern and Northern blot analysis and for nylon membrane-based macroarrays. There is a need for improved hybridization rates in order to expedite HTS methods and for other purposes. The present invention satisfies this need by providing nucleic acid hybridization rate enhancement (HRE) methods.

BRIEF SUMMARY OF THE INVENTION

The invention relates to a method of hybridizing a nucleic acid and a specific nucleic acid-binding agent (SNABA). The method comprises contacting, in the presence of a binding solution,
  i) the nucleic acid and
  ii) a substrate (e.g., a porous or non-porous glass, silicon, or plastic substrate) having a hybridization region.

The SNABA and a polycationizable attractor compound (PCAC) are bound (e.g., covalently) to the substrate in the hybridization region. The PCAC comprises at least two moieties that are positively charged at the pH of the binding solution, including at least one cationizable moiety having a pK value in the pH range 4 to 9.5. Preferably, the substrate also has one or more of a background region to which neither the SNABA nor the PCAC is bound, a first control region to which the SNABA is bound and to which the PCAC is not bound, and a second control region to which the PCAC is bound and to which the SNABA is not bound.

In one embodiment, the molar amount of the SNABA bound to the hybridization region is about equal to the molar amount of the PCAC bound to the hybridization region, or at least not more than about three times the molar amount of the SNABA bound to the hybridization region.

In another embodiment, the PCAC comprises at least five, ten, or fifteen moieties that are positively charged at the pH of the binding solution. The PCAC preferably does not comprise a moiety that is negatively charged at the pH of the binding solution. The PCAC can be a polypeptide, such as one that comprises not more than 25 amino acid residues (preferably from 5 to about 20 or from 10 to 20 amino acid residues). When the PCAC is a polypeptide, its carboxyl terminus can be capped (e.g., amidated or conjugated with the SNABA.). Polypeptide PCACs preferably comprise at least one histidine residue, at least one lysine residue, or both. Examples of polypeptide PCACs include polypeptides that comprises a region having the amino acid sequence of one of SEQ ID NOs: 1, 2, and 9–22 (preferably one of SEQ ID NOs: 16–18) and polypeptides that have the amino acid sequence of one of SEQ ID NOs: 1, 2, and 9–22 (preferably one of SEQ ID NOs: 16–18). In one embodiment, the molecular weight of the PCAC is not greater than about 15000.

The substrate-bound PCAC can have the chemical structure

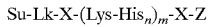

wherein
  Su is the substrate;
  Lk is a linker;
  each X is independently 0 to 25 amino acid residues;
  n is 1 to 5;
  m is 1 to 10; and
  Z is one of a hydrogen radical, a carboxylate capping moiety, and the SNABA.

The linker can, for example, be a covalent bond or an N-hydroxysuccinimidyl moiety. The amino acid residues of the X moieties preferably are residues that have side chains that are not negatively charged at the pH of the binding solution. Furthermore, if any of the amino acid residues of the X moieties have a side chain carboxylate moiety, then that side chain carboxylate moiety can be capped. If Z is an amide moiety, appropriate chemical structures include $-NR^1R^2$, wherein each $R^1$ and $R^2$ is independently selected from the group consisting of a hydrogen radical and $C_1-C_6$ straight chain alkyl radicals, optionally substituted with one or more hydroxyl or amine moieties and $-NR^3R^4$, wherein $R^3$ and $R^4$ are together a $C_5-C_8$ dialkylene moiety, optionally substituted with one or more hydroxyl or amine moieties. In one embodiment, Z is $-NH_2$.

The substrate-bound compound can have the chemical structure:

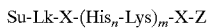

wherein the moieties have same definitions described above.

In an important embodiment, the SNABA is a polynucleotide, such as one that is complementary to the nucleic acid. Other potential SNABAs include polynucleotide analogs, sequence-specific nucleic acid-binding proteins, structure-specific nucleic acid-binding proteins, and conformation-specific nucleic acid-binding proteins. The SNABA can be conjugated (e.g., covalently) with the PCAC.

After contacting the substrate and the binding solution, the substrate can be contacted with a second binding solution, wherein the pH of the second binding solution is greater than the pH of the binding solution. In one embodiment, the binding solution is removed and replaced by the second binding solution. In another embodiment, a pH modifying agent is added to the binding solution to yield the second binding solution. Preferably, the net charge of the PCAC is less positive in the presence of the second binding solution than in the presence of the binding solution. For example, the second binding solution can be selected such that the net positive charge of the PCAC in the presence of the second binding solution is not more than half (or not more than one-fourth) the net positive charge of the PCAC in the presence of the binding solution. Instead, or in addition, the ionic strength of the second binding solution can be greater than the ionic strength of the binding solution.

The substrate can be contacted with a first rinse solution after contacting the substrate with the second binding solution, wherein the first rinse solution has a different temperature than the second binding solution.

The invention also relates to a device for hybridizing a nucleic acid and a specific nucleic acid-binding agent (SNABA) in the presence of a binding solution. The device comprises a substrate having a hybridization region. The hybridization region has bound thereto
i) the SNABA and
ii) a polycationizable attractor compound (PCAC).

The PCAC comprises at least two moieties that are positively charged at the pH of the binding solution, including at least one cationizable moiety having a pK value in the pH range 4 to 9.5. The invention includes a kit for hybridizing a nucleic acid and a SNABA. The kit comprising this device and an instructional material that describes using the device to hybridize the nucleic acid and the SNABA.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

FIG. 1 comprises FIGS. 1A and 1B.

FIG. 2 comprises FIGS. 2A and 2b.

FIG. 6 comprises FIGS. 6A, 6B, and 6C.

DETAILED DESCRIPTION OF THE INVENTION

Figures 1A, 1B:
FIG. 1A is an image of a peptide array described in Example 2, under fluorescing conditions.
FIG. 1B is a map showing the arrangement of peptides spotted on the array shown in FIG. 1A.

Conventional nucleic acid hybridization is passive and relies on the slow diffusion and association kinetics of i) a nucleic acid target molecule (a target) suspended in a fluid and ii) a second molecule (a probe) that can be suspended in the fluid or fixed at a surface contacted by the fluid. Passive hybridization rates depend heavily on the concentration of the target in the fluid, although they also depend on other factors (e.g., probe concentration, target and probe structures, temperature, and ionic strength of the fluid).

The present invention relates to a hybridization technique that can significantly accelerate hybridization rates, relative to passive hybridization methods. The methods disclosed herein are referred to generally as hybridization rate enhancement (HRE) methods, and involve inducing an electrostatic charge to a substrate to which a specific nucleic acid binding agent (SNABA; e.g., a nucleic acid probe, a nucleic acid-binding protein, or another nucleic acid-binding substance) is bound in order to attract a target to the substrate. Unlike previous methods, in which charged substrates were used in order to attract target polynucleotides generally to the entire surface area of the substrate, HRE methods described herein involve inducing a charge only at one or more regions of the substrate at which a SNABA occurs (possibly including one or more 'contro' regions at which the charge is induced in the absence of a SNABA). Using HRE methods described herein, nucleic acid hybridization times can be significantly reduced.

Whereas prior art hybridization methods can require hybridization periods of hours or days, hybridization methods comprising the HRE methods described herein can yield sufficient hybridization in as little as about 1, 2, 3, 5, 10, 15, 20, 30, or 45 minutes. Depending on the amount of hybridization needed (e.g., when using easily detected nucleic acids), even shorter hybridization periods (e.g., 1, 2, 3, 5, 10, 15, 20, 30, or 45 second) can be employed. These reduced hybridization periods represent a dramatic improvement over prior conventional hybridization methods. Hybridization assays employing HRE methods can yield real-time hybridization results.

Others (e.g., U.S. Pat. No. 6,331,274) have constructed devices intended for enhancing hybridization rates. These devices comprise miniaturized electronic circuits that have electrodes disposed at or near sites of intended nucleic acid hybridization. Such devices require complicated and expensive fabrication methods, intricate circuit design and layout, and are relatively limited in the numbers of interrogable hybridization spots that can be placed on a single device. Furthermore, these devices require expensive and highly specialized equipment for their operation and analysis, including mechanisms for regulating and distributing electrical current. The apparatus and methods described herein do not have these drawbacks.

The nucleic acid HRE methods disclosed here comprise contacting a nucleic acid and a substrate having a SNABA bound thereto in the presence of a binding solution. In addition to the SNABA, the substrate also has a polycationizable attractor compound (PCAC) bound thereto. Preferably, the PCAC and the SNABA are bound to the same region of the substrate, preferably in an interspersed fashion. That is, a hybridization region of the substrate has both the PCAC and the SNABA bound thereto, either in an ordered or a disordered arrangement. The PCAC has at least two moieties (e.g., amino acid side chains) that are positively charged at the pH of the binding solution.

In the presence of the binding solution, the PCAC has a positive charge in the hybridization region of the substrate, and the nucleic acid is attracted to the hybridization region. Without being bound by any particular theory of operation, it is believed that attraction of the nucleic acid to the hybridization region increases the effective local concentration of the nucleic acid at the hybridization region. Because the SNABA is also present at the hybridization region, the increased effective local concentration of the nucleic acid enhances the rate of hybridization of the nucleic acid and the SNABA, thereby enhancing the hybridization rate of the method and decreasing the amount of time necessary to achieve hybridization.

In one example of the method, a first nucleic acid can be contacted with a substrate having a PCAC and a second nucleic acid (the SNABA in this example) bound to region thereof. If the first and second nucleic acids have complementary sequences, they can hybridize. The presence of the PCAC in the hybridization region of the substrate enhances the rate at which complementary first and second nucleic acids hybridize, relative to the rate at which they would hybridize in a method using a substrate that does not have the PCAC bound to its hybridization region.

An additional benefit of the HRE methods described herein is that they facilitate hybridization methods involving detection of nucleic acids that are present in a sample at a much lower concentrations than would be practical using prior conventional hybridization methods. Presumably owing to the nucleic acid-concentrating effect of the PCAC at the hybridization region, hybridization reactions that would be impracticably slow using prior conventional hybridization methods can be accelerated such that the reaction can be completed in a reasonable time (seconds, minutes, hours, or days).

The PCAC can be present on the entire surface of the substrate that is contacted with the binding solution, although it preferably is present only in one or more regions in which a SNABA is present. Of course, the PCAC can be present at portions of the substrate at which the SNABA is not present, in order to provide a control region that can be compared with a hybridization region at which both the PCAC and SNABA are present, so that the specificity of nucleic acid for the SNABA (relative to the PCAC) can be assessed. Alternatively, the PCAC can be present at only some regions of the substrate at which the SNABA is present, or the PCAC can be present at a greater concentration at SNABA-containing regions than at regions of the substrate at which the SNABA is not present.

Definitions

As used herein, each of the following terms has the meaning associated with it in this section.

A nucleic acid "hybridizes" with an agent if the nucleic acid binds non-covalently with the agent only if the nucleic acid has a sequence, structure, or conformation that characterizes the binding ability of the agent. By way of example, a first nucleic acid is characterized in that it will bind specifically with nucleic acids which exhibit a region of significant sequence complementarity.

A "polycationizable attractor compound" ("PCAC") is a compound having at least two positively charged moieties at the pH of a binding solution used in a method described herein, including at least one cationizable moiety with a pK value of 4 to 9.5 (preferably 4 to 8). In one embodiment, the PCAC has a molecular weight of at least about 200 and not greater than about 15000. By way of example, polypeptides (and their analogs) comprising from about 2 to 100 amino acid residues can be used as PCACs, provided they comprise at least two amino acid residues having side chains that are positively charged at the pH of the binding solution, including one having a pK value of 4 to 9.5 (preferably 4 to 8). Streptavidin is an example of a polypeptide that is suitable for use as a PCAC.

A "specific nucleic acid binding agent" ("SNABA") is a compound that binds specifically with a nucleic acid if the nucleic acid comprises a portion having a defined sequence, structure, or conformation. Examples of SNABAs include nucleic acids (i.e., which bind specifically with nucleic acids having complementary sequences), sequence-specific nucleic acid binding proteins (e.g., the lac repressor protein of the *Escherichia coli* lac operon, which binds specifically with DNA having the sequence of the lac operator region), and structure- or conformation-specific nucleic acid binding proteins (e.g., *E. coli* MutS protein and its mammalian homologs, which bind with mismatched DNA).

An "amplicon target" is a DNA target molecule generated by polymerase chain reaction (PCR) amplification of a template DNA (e.g., plasmid DNA and genomic DNA) or cDNA (e.g., reverse transcribed from an RNA sample).

A "probe-spot" is an individual location (or address) on an array surface to which a SNABA, a PCAC, or both, occur.

A "background" region is an area of a substrate to which no nucleic acid probe is bound. For example, a background region can be the substrate area defined by the space between individual probe-spots on a hybridization region of a substrate.

A "control" region is an area of a substrate to which not more than one of a SNABA and a PCAC is bound, and is useful for comparing binding attributable to one or both of the SNABA and the PCAC with binding that is not dependent on the presence of the SNABA or on the presence of the PCAC.

A "co-print ratio" refers to the ratio of SNABA to PCAC in a suspension that is applied to a substrate at a probe-spot. For example, a probe-spot having a co-print ratio of 1:2 can be achieved by applying a solution comprising 2 PCAC molecules for every 1 molecule of SNABA in the suspension.

A "co-binding ratio" refers to the ratio of SNABA to PCAC that occurs at a probe spot on a substrate. For example, a probe-spot having a co-binding ratio of 1:2 has 2 PCAC molecules bound at the probe spot for every 1 molecule of SNABA bound at the probe spot. As described herein, application of a suspension comprising a SNABA and a PCAC at a certain co-print ratio does not necessarily result in a probe spot having the same co-binding ratio (e.g., owing to potential differences in the reactivity of the SNABA and the PCAC for potential binding sites on the substrate).

A chemical compound or moiety is "cationizable" if the compound or moiety exhibits a positive charge at one pH and is uncharged at a higher pH.

A chemical compound or moiety is "polycationizable" if the compound or moiety exhibits a positive charge of at least +2 at one pH and a less positive charge at a higher pH.

"Complementary" refers to the broad concept of subunit sequence complementary between two nucleic acids, e.g., between two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%, 70%, 90%, or 100%) of corresponding positions in each of the molecules are occupied by nucleotides which normally base pair with each other (e.g., A:T and G:C nucleotide pairs).

An "instructional material" is a publication, a recording, a diagram, or any other medium of expression which can be used to communicate how to use a kit or method described herein. The instructional material of a kit of the invention can, for example, be affixed to a container that contains a kit of the invention or be shipped together with a container which contains a kit. Alternatively, the instructional material can be shipped separately from the container with the intention that the instructional material and the kit be used cooperatively by the recipient.

Description

The invention relates to compositions, kits, and methods for enhancing the rate at which a nucleic acid binds specifically (hybridizes) with an agent. The agents are herein designated specific nucleic acid binding agents (SNABAs) to highlight that the binding between the nucleic acid is not merely non-specific adsorption of two molecules, but rather an interaction that depends on the sequence, structure, or conformation of the nucleic acid. The SNABA is bound with a substrate, and the substrate is contacted, in the presence of a binding solution, with a sample comprising the nucleic acid in order to facilitate hybridization of the SNABA and the nucleic acid, as in prior art methods. However, in the enhanced compositions, kits, and methods described herein, a second compound is also bound with the substrate. This compound, designated a polycationizable attractor compound (PCAC), has multiple positively-charged moieties at the pH of the binding solution. The SNABA and the PCAC are bound to the same region of the substrate, and the rate of hybridization of the nucleic acid and the SNABA is higher when the PCAC is bound with the substrate than when the PCAC is not bound with the substrate. Thus, an enhanced rate of hybridization is achieved using a substrate having both the SNABA and the PCAC bound thereto.

After contacting the nucleic acid and the substrate in the presence of the binding solution, the pH of the binding solution can be raised (or the binding solution can be replaced with a second binding solution having a higher pH). As the pH rises (e.g., from a pH<6 to a pH>6, such as a pH change from 4 to 8 or from 5 to 7), the positive charge of the PCAC decreases, because the PCAC comprises a cationizable residue having a pK value in the range from 4 to 9.5 (preferably 4 to 8; e.g., histidine residue side chains have a pK value of 6.0). As the pH rises, the influence of the PCAC on binding of the nucleic acid with the substrate decreases, and the specificity of binding of the nucleic acid with the substrate approaches the specificity of hybridization between the SNABA and the nucleic acid. Alternatively, or in addition, the second binding solution can have a higher ionic strength, a higher temperature, or both, in order to minimize non-specific binding of the nucleic acid with the substrate. The binding solution can be aspirated or decanted from the substrate, the substrate can be rinsed with a liquid to displace non-specifically bound nucleic acids, or both prior to detecting bound nucleic acids.

As a specific example of how the hybridization reaction can be performed, a substrate having a PCAC and a SNABA bound thereto can be contacted with a nucleic acid in the presence of a selected volume of a binding solution that consists essentially of 2 millimolar buffer (e.g., acetate buffer) at pH 4.5. After several seconds or minutes, an approximately equal volume of standard saline citrate buffer (pH 7.5) can be combined with the binding solution in order to raise the pH thereof to about 7.5.

Without being bound by any particular theory of operation, it is believed that as the positive charge of the PCAC decreases, the extent to which association of the nucleic acid with the substrate is dependent on non-specific charge attraction between the nucleic acid and the PCAC decreases. So long as the PCAC does not specifically bind with the nucleic acid, the PCAC's contribution to nucleic acid-substrate association should become minimal or zero as the charge on the PCAC approaches neutrality. Theoretically, when the PCAC is non-charged, the specificity of binding of the nucleic acid and the substrate should be entirely dependent on the SNABA. Thus, the presence of the PCAC can concentrate the nucleic acid near the substrate (and near the SNABA), but should not affect the specificity of nucleic acid-SNABA hybridization. The result is that the hybridization reaction is accelerated without altering its specificity.

The compositions, kits, and methods described herein can be used to enhance the speed at which assays relying on nucleic acid hybridization with an agent can be performed. Speed can be of significant concern in situations in which large numbers of assays need to be performed in minimal time, such as in high-throughput screening applications. The subject matter disclosed herein is amenable to use in high-throughput screening assays in which hybridization of a nucleic acid and a SNABA are assessed, because the SNABA and the PCAC can be simultaneously or sequentially incorporated into the same assay materials and apparatus that are presently used. By way of example, microarrays comprising a substrate having numerous hybridization regions, wherein individual hybridization regions have a single SNABA bound thereto (e.g., nucleic acid probe arrays) are commonly used in high-throughput screening assays. The invention includes improved microarrays in which at least some (and preferably all) of the hybridization regions also have a PCAC bound thereto. The period for which an improved microarray needs to be contacted with a nucleic acid-containing sample in order to achieve hybridization of the nucleic acid and the SNABA(s) can be significantly shorter than the corresponding period for microarrays not comprising a PCAC.

The Specific Nucleic Acid-Binding Agent (SNABA)

The identity of the SNABA is not critical. Numerous SNABAs are known in the art, including polynucleotides, polynucleotide analogs, sequence-specific nucleic acid binding proteins, structure-specific nucleic acid binding proteins, and conformation-specific nucleic acid binding proteins. Polynucleotide analogs include those with which a naturally-occurring type of nucleic acid (e.g., DNA or RNA) can hybridize. Examples of polynucleotide analogs include polymers of deoxyribonucleosides, ribonucleosides, or both, and having non-naturally-occurring inter-nucleoside linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. Polynucleotide analogs also need not be composed of only the five naturally-occurring bases (adenine, guanine, thymine, cytosine and uracil), but can include other bases instead or in addition (e.g., inosine). Substitution of non-naturally-occurring bases in place of naturally-occurring ones, and the corresponding effects on binding specificity are known in the art.

In a preferred embodiment, the SNABA is a polynucleotide that binds with the nucleic acid in a complementary sequence-dependent fashion. By way of example, the polynucleotide can have approximately the same length as the nucleic acid and sequence that is at least substantially complementary to the sequence of the nucleic acid along its entire length. Alternatively, the polynucleotide can have a first portion that has a sequence that is substantially complementary to some or all of the nucleic acid and a second portion that is not.

In one embodiment, the substrate has a polynucleotide (i.e., the SNABA) and a PCAC bound thereto. The polynucleotide is complementary to a portion of a labeled cDNA or to a portion of a PCR product generated when a cDNA corresponding to a selected gene is amplified using particular primers. The substrate can be used to assess whether a cell expresses the gene by making a cDNA preparation from the cell, amplifying the cDNA so generated using the particular primers, and contacting the amplified products (i.e., nucleic acids) with the substrate. Hybridization of the amplified product with the substrate is an indication that the gene is expressed in the cell. This type of assay has use in assessing the tissue, or cell-type, specificity of gene expression, the ontology of gene expression in a single cell type, the difference in gene expression between diseased and non-diseased tissues, and for other purposes.

Hybridization of nucleic acids with SNABAs was previously known. However, the kinetics of conventional prior art methods of performing such hybridizations are often slow, and require hybridization periods of hours, days, or longer. The methods described herein significantly enhance the rate at which hybridization reactions occur. As a result, hybridization reactions can be performed more quickly, and hybridization periods can be significantly shorter (seconds, minutes, hours, or days). By way of example, prior conventional hybridization methods involving very dilute samples of a nucleic acid often required hybridization periods so long that the procedure was not practical. With the hybridization rate enhancement technology described herein, these hybridizations can be performed much more quickly.

The Polycationizable Attractor Compound (PCAC)

The identity of the PCAC is not critical. However, the PCAC should be a molecule that, when it is bound with the substrate and exposed to the binding solution, has at least two positively charged moieties, although it can have more (e.g., 3 to 25, such as 3, 4, 5, 7, 10, 15, or 20) positively charged moieties. At least one of the positively charged moieties should be a cationizable moiety having a pK value in the range from 4 to 9.5 (preferably in the pH range from 4 to 8, and more preferably around 6). At pH values below the pK value, the cationizable moiety tends to be positively charged, and at pH values above the pK value, this moiety tends to be non-charged (i.e., neutral). Cationizable moieties are "tunable," such that the net charge on the PCAC can be controlled by modulating the pH of the solution that contacts the PCAC. The PCAC preferably contains numerous cationizable moieties, so that a greater range of net charge states can be generated by modulating solution pH.

The tunable nature of the positive charge of a substrate-bound PCAC facilitates attraction of nucleic acids (which are ordinarily negatively charged) to the substrate at relatively low pH values (i.e., a pH at which the PCAC exhibits a large positive charge). Because the net charge on the PCAC is tunable, some or all of the positive charge of the PCAC can be neutralized (e.g., by raising the pH of the solution that contacts the substrate) in order to reduce interference by the PCAC with hybridization between nucleic acids attracted to the substrate and a SNABA bound to the substrate.

The size and charge density of the PCAC are not critical. In one embodiment, the molecular weight of the PCAC is preferably not less than about 200, and preferably not greater than about 15000. It is possible that compounds having a molecular weight lower than 200 will be substantially obscured by the SNABA, the substrate, or both. Compounds having molecular weights greater than 15000 can sometimes interfere with binding between the nucleic acid and the SNABA, so smaller compounds can be preferable. Polypeptides (i.e., amino acid polymers having two or more amino acid residues or their analogues) can be used as PCACs, provided they comprise the cationizable moieties described herein. One example of such a polypeptide is streptavidin. Other suitable polypeptides are described herein.

Nucleic acid hybridization assays are often performed in solutions having pH values in the range from 4 to 9.5 (more commonly in the range from 4 to 8) for a variety of reasons. The PCAC preferably has a cationizable moiety that has a pK value within this range, and preferably toward the center of the range. Histidine residues of polypeptides have a pK value for the imidazole side chain moiety that has a value of about 6.0. Thus, compounds comprising one or more histidine moieties (or other types of imidazoyl moieties) are useful as PCACs in many assay conditions.

A preferred class of PCACs are polypeptides, including polypeptide analogs and peptidomimetics. When the PCAC is a polypeptide, it preferably has a length not less than 4 or 5 amino acid residues, and preferably has a length not greater than about 100 amino acid residues. Longer polypeptides can adopt secondary or tertiary structures that can obscure positively charged residues. In the pH range from 4 to 9.5, both lysine and histidine residue side chains can be positively-charged. Lysine side chains are positively charged substantially throughout this pH range. At pH 6.0, approximately half of histidine side chains are positively charged, and half are non-charged. At lower pH values, a greater proportion of histidine side chains are positively charged, and at higher pH values, a smaller proportion are positively charged. Thus, histidine residues confer charge "tunability" to polypeptides, and their inclusion in polypeptide PCACs is preferred. In some embodiments, the polypeptide includes amino acid residues (e.g., lysine residues) that have side chains that are positively charged throughout the pH range 4 to 9.5 (preferably 4 to 8).

PCACs having positively-charged amino acid residues can confer a number of benefits to the PCAC. The positively-charged residues can increase the solubility of the PCAC, thereby potentially improving its ability to interact with the target nucleic acid. The positively-charged residues can neutralize, mask, or overcome any negatively-charged moieties that exist on the substrate, which could otherwise repel the target from the surface of the substrate, thereby inhibiting binding between the target nucleic acid and the SNABA. Similarly, the positively-charged moieties of the PCAC can reduce the repulsive effects of any negatively-charged moieties of the SNABA and negative charges of the target nucleic acid, thereby reducing repulsion between the target and the SNABA and enhancing binding of the two.

When the PCAC is a polypeptide, it is preferably bound to the substrate at one of its linear ends—that is, at either the amino terminus or the carboxyl terminus of the polypeptide. When the polypeptide is bound at its amino terminus, the carboxyl terminus should be capped in order to neutralize or eliminate its inherent anionizability. One preferable way of capping a polypeptide PCAC (or substantially any other PCAC) is by conjugating the SNABA to a linear end of the PCAC. By way of example, if the PCAC is a polypeptide and the SNABA is a polynucleotide, the SNABA can be conjugated with the carboxyl terminus of the polypeptide, and the amino terminus of the polypeptide can be bound to the substrate.

In one embodiment, the PCAC has the chemical structure of either Formula I or Formula II, as follows.

$$\text{Su-Lk-X-(Lys-His}_n)_m\text{-X-Z} \quad (I)$$

$$\text{Su-Lk-X-(His}_n\text{-Lys)}_m\text{-X-Z} \quad (II)$$

In each of Formulas I and II:
Su is the substrate;
Lk is a linker;
each X is independently 0 to 25 amino acid residues;
n is 1 to 5 (or higher, e.g., 7, 10, 15, 20, 25);
m is 1 to 10 (or higher, e.g., 15, 20, 50, 100); and
Z is a hydrogen radical, a carboxylate capping moiety, or the SNABA.

In Formulas I and II, the carboxylate capping moiety can be substantially any relatively small group (the group generally having a molecular weight not greater than about 300) that renders the carboxyl terminal carboxyl moiety incapable of becoming negatively charged or that at least raises the pK of any carboxyl terminal anionizable moiety about two pH units higher than the pH of the binding solution (i.e., the capping moiety prevents the carboxyl terminus from being negatively charged). An appropriate carboxyl capping moiety is an amide moiety or a methyl moiety. When Z is an amide moiety, one appropriate structure for Z is —NR$^1$R$^2$, wherein each R$^1$ and R$^2$ is independently selected from the group consisting of a hydrogen radical and C$_1$–C$_6$ straight chain alkyl radicals, optionally substituted with one or more hydroxyl or amine moieties. Another appropriate structure for Z is —NR$^3$R$^4$, wherein R$^3$ and R$^4$ are together a C$_5$–C$_8$ dialkylene moiety, optionally substituted with one or more hydroxyl or amine moieties. As noted above, Z can be the SNABA, conjugated to the PCAC.

In Formulas I and II, each X represents a spacer polypeptide region that comprises 0 to 25 amino acid residues. Each of the residues in the spacer polypeptide regions can be any amino acid residue, but the residues are preferably not negatively charged at the pH of the binding solution. The residues can be non-charged or positively-charged. In one embodiment, one or more of the residues have cationizable moieties with a pK value in the pH range from 4 to 9.5 (preferably in the pH range from 4 to 8). For example, polypeptide PCACs preferably either do not comprise glutamate and aspartate residues or, if they do comprise such residues, then the beta- and gamma-carboxyl moieties of these residues are capped in order to prevent the side chains from being negatively charged at the pH of the binding solution.

Examples of polypeptides that are useful as PCACs are disclosed herein, and have sequences that either comprise one of SEQ ID NOs: 1, 2, and 9–22 (preferably comprising one of SEQ ID NOs: 16–18) or are identical to one of SEQ ID NOs: 1, 2, and 9–22 (preferably identical to one of SEQ ID NOs: 16–18).

The Substrate

The identity of the substrate is not critical, except that it should comprise a material to which the SNABA and the PCAC can be bound (directly or indirectly). The substrate preferably does not exhibit significant binding of nucleic acids, so that binding of a nucleic acid in the hybridization region depends on the presence of the SNABA in that region. Examples of suitable substrates include glasses, plastics, silicon substrates, and other materials used in fabrication of biomolecule microarray devices.

The substrate can be porous, but is preferably substantially impermeable to the binding solution, so that the SNABA and the PCAC are bound substantially only at the surface of the substrate that contacts the binding solution. Examples of porous surfaces include polyacrylamide gels and other hydrogels. When porous substrates are used, the pore size of the substrate is preferably large in comparison with the size (e.g., hydrodynamic diameter) of the nucleic acid to be hybridized with the SNABA, so that mass transport limitations do not interfere with hybridization of the nucleic acid and the SNABA.

The way in which the SNABA and the PCAC are bound with the hybridization region of the substrate is not critical, and can depend on the identity of the SNABA or PCAC. By way of example, it is known that substrates having N-hydroxysuccinimidyl ester moieties (e.g., AFFIGEL™ products, Bio-Rad Laboratories, Richmond, Calif.) can be coupled with polynucleotides and polypeptides having free primary amine moieties. Similarly, it is known that substrates having iodoacetamide moieties (e.g., SUL-FOLINK™ products, Pierce Chemical Company, Rockford, Ill.) can be coupled with agents having free sulfhydryl moieties (e.g., cysteine side chains). Numerous other compositions and methods for binding polynucleotides, polynucleotide analogs, polypeptides, and polypeptide analogs with various substrates are known. The choice of a coupling agent appropriate for binding the SNABA and PCAC with the substrate is within the ordinary level of skill in the art.

The SNABA and the PCAC are each preferably bound covalently with the substrate, although non-covalent means of binding them (e.g., using antibodies, biotin-streptavidin attraction, or hydrophobic association) can also be used. In one embodiment, the SNABA and the PCAC are conjugated, and one or both is bound to the substrate. Polymers of conjugated SNABAs and PCACs can also be bound with the substrate. As examples, suitable configurations of conjugated SNABAs and PCACs include the following:
substrate-PCAC-SNABA;
substrate-SNABA-PCAC;
substrate-PCAC-SNABA-PCAC;
substrate-SNABA-PCAC-SNABA; and
substrate-SNABA-PCAC-SNABA-PCAC.

One convenient form of the substrate is a flat surface. Microarrays of biomolecules are routinely synthesized, printed, or otherwise applied in distinct hybridization regions on flat surfaces, so that a sample can be applied to the surface and simultaneously contact each of the distinct hybridization regions. Numerous methods of making such surfaces are known, including methods in which the biomolecules are synthesized on the surface using lithography techniques, photo-deposition techniques (e.g., mask-less array synthesis), methods in which biomolecules are printed on the surface using contact spotters (e.g., pin and capillary systems) or non-contact spotters (e.g., ink jet or piezo-electric printing/deposition systems). Flat surfaces can facilitate all of these manufacturing methods.

The substrate can be a unitary piece of material having one or more hybridization regions to which both an individual SNABA and the PCAC are bound. The substrate can be unitary and have multiple hybridization regions having different SNABAs bound individual thereto (together with the PCAC). The substrate can have the form of a particle, wherein the particle has only a single SNABA bound thereto (together with the PCAC). A plurality or multiplicity of such particles can be used simultaneously with a single sample in order to hybridize nucleic acids in the sample with individual particles.

The substrate has at least one hybridization region at which both a SNABA and a PCAC are bound. The substrate preferably has a background region to which neither the SNABA nor the PCAC is bound, and this background region is preferably adjacent (abutting) a hybridization region, so that contrast between nucleic acid binding at the hybridization region and the background region can be easily observed. The substrate can have one or more control regions at which only one of the SNABA and the PCAC are bound (i.e., both are not bound at the same control region). These control regions can be used to assess nucleic acid binding to the substrate that is not attributable to the omitted SNABA or PCAC.

Within individual hybridization regions, the relative amounts of the SNABA and the PCAC that are bound to individual regions can vary. The optimal ratio of SNABA and PCAC amounts in a region are best determined experimentally, since the optimal ratio can vary based on a number of factors, including the characteristics of the nucleic acid and the SNABA, the size of the PCAC, the charge of the PCAC at the pH of the binding solution, the geometry of the assay system, the temperature at which the hybridization is performed, the concentration of desired nucleic acid in the sample, and the concentration of non-desired (non-SNABA-binding) nucleic acid in the sample. Determining an appropriate ratio of SNABA and PCAC in a hybridization region can be done simply by preparing several hybridization regions having varying ratios of SNABA and PCAC amounts, performing a hybridization under simulated (or actual) assay conditions, and assessing the degree of specific nucleic acid binding at each of the experimental regions. As a general rule, the molar ratio of SNABA/PCAC that should be used for a hybridization assay will decrease as the number of charged moieties present on the PCAC at the pH of the binding solution increases. By way of example, it has been determined that when hybridization is performed for a nucleic acid having a length of about 15 nucleotide residues and a polynucleotide (SNABA) having approximately the same length is desired at a hybridization region to which a PCAC having 15 positively-charged moieties at the pH of the binding solution, desirable molar ratios of (SNABA)/(PCAC) can be in the approximate range from 0.5 to 2. However, the range of desirable co-binding ratios can vary depending on the experimental conditions used (e.g., depending on the composition of the binding solution). Furthermore, co-print ratios needed to achieve those co-binding ratios will depend on the nature of the substrate, the chemistry by which the SNABA and the PCAC are attached to the substrate, any interactions between the SNABA and the PCAC, potential effects of the printing or spotted method used, and other factors. However, empirical selection of appropriate co-binding and co-print ratios is within the ken of the ordinarily skilled artisan in view of the guidance provided herein.

The size of the hybridization region to which the SNABA and the PCAC are bound is not critical. However, it is important that the SNABA and the PCAC be bound sufficiently closely within the hybridization region that nucleic acids attracted by non-specific charge-based forces to the PCAC are effectively concentrated nearby the SNABA binding sites on the substrates. Thus, the average distance between SNABA binding sites and PCAC binding sites on the hybridization region should generally not be greater than about 50 to 100 Angstroms (i.e., about the maximum distance across which electrostatic effects have an effect in relatively low ionic strength solution), and preferably not greater than about 20 Angstroms. Preferably, the SNABA and the PCAC are simultaneously bound (e.g., bound using the same reaction solution comprising both the SNABA and the PCAC) to the substrate, so that the SNABA and PCAC molecules are randomly distributed within the hybridization regions. However, SNABA molecules and PCAC molecules can be separately bound to the substrate, in various geometrical configurations (e.g., SNABA spots surrounded by PCAC rings, alternating stripes of SNABA and PCAC, etc.) if desired. Because the hybridization rate-enhancing effect attributable to co-localization of the SNABA and the PCAC is believed to be attributable to a nucleic acid-concentrating effect exerted by the PCAC, it is important that SNABA molecules be physically located near enough to PCAC molecules that the concentrating effect is not substantially reduced by diffusion of nucleic acid molecules away from the PCAC molecules. So long as the SNABA and PCAC molecules are sufficiently close to one another, diffusion of nucleic acid molecules from the PCAC molecules to the SNABA molecules will be much greater than diffusion of the nucleic acid away from the SNABA, so diffusion effects should not overwhelm the nucleic acid-concentrating effects achieved using the PCAC.

As an example of a method by which SNABA and PCAC molecules can be simultaneously bound to a hybridization region, reference is made to U.S. Pat. No. 6,331,441, wherein methods and devices for spotting samples onto array substrates are disclosed. The methods in that patent or any other similar reference can be used to spot a suspension comprising both the SNABA and PCAC onto a substrate in a reproducible or addressable manner.

The Nucleic Acid

The identity of the nucleic acid that is to be hybridized with the SNABA is not critical. Nucleic acids that can be used include naturally-occurring polynucleotides, synthetic polynucleotides, amplified polynucleotides, antisense polynucleotides; ribozymes; viral polynucleotides; chimeric polynucleotides; mRNA; plasmids; cosmids; genomic DNA; cDNA; gene fragments; and various structural forms of polynucleotides including single-stranded, double-stranded, supercoiled, triple-helical, and mismatched polynucleotides. The nucleic acid can be isolated or prepared by any conventional means.

The Binding Solution

The identity of the binding solution in the presence of which the nucleic acid and the substrate are contacted is not critical. Substantially any fluid in which a nucleic acid can be hybridized with a SNABA can be used. Common examples of binding solutions include standard saline citrate buffer and dilutions thereof, PCR product solutions, and crude or de-proteinized cell extracts.

The binding solution has a pH such that the PCAC has more than one (preferably at least two, five, ten, or fifteen, on average) charged moieties. In this respect, the pH of the binding solution and the cationizable characteristics of the PCAC are interrelated, and the two can be selected in substantially any combination wherein this pH/charge relationship holds. By way of example, if the PCAC comprises one moiety that is fully positively-charged at the pH of the binding solution (i.e., the pK of the moiety is at least about two pH units above the pH of the binding solution) and the PCAC comprises cationizable moieties having a pK value about equal to the pH of the binding solution (i.e., about 50% of those moieties will be positively charged at the pH of the binding solution), then the PCAC should comprise at least two of those cationizable moieties, so that the PCAC will have an average charge of about +2 or greater at the pH of the binding solution.

Components of the binding solution can interfere with attraction between the nucleic acid and the PCAC, thereby reducing enhancement of the hybridization rate. These components include those which increase ionic strength of the binding solution, those that increase the viscosity of the binding solution, nucleic acid denaturing agents, and charged molecules. The concentration of these components in the binding solution should therefore be maintained as low as practical or possible.

Interaction between oppositely charged molecules (e.g., PCACs and nucleic acids) is dependent on the attraction between opposite electrostatic charges over a distance in solution. It is known that increasing the ionic strength of a solution inhibits attraction between oppositely charged molecules in the solution. For this reason, the binding solution preferably has a low ionic strength, so that hybridization rate enhancement effected by attraction between the nucleic acid and the PCAC is minimally inhibited.

Displacement of a nucleic acid from a position in a solution distant from a PCAC to a position nearer the PCAC requires movement of the nucleic acid through the solution (i.e., equivalent to flow of the solution around the nucleic acid). The viscosity of a liquid describes the liquid's resistance to flow, and hence resistance of a molecule therethrough. Increasing the viscosity of a solution inhibits movement of a nucleic acid through it, increasing the amount of time required for the same degree of movement. Thus, increasing viscosity of the binding solution will decrease the hybridization rate enhancement effected by the presence of the PCAC on the substrate. For this reason, the viscosity of the binding solution should be as low as practical or possible.

Compounds that denature nucleic acids (e.g., DMSO and formamide) induce structural changes in the nucleic acid that increase its size (and corresponding hydrodynamic diameter) in solution. Consequently, movement of a nucleic acid through a solution will generally be slower in the presence of such denaturing agents than in their absence, and such movement will be inhibited as the concentration of denaturing agents increases, at least over a certain range of concentrations. Because inhibition of nucleic acid movement through a solution would decrease hybridization rate enhancement effected in the methods described herein, it is preferable that the binding solution contain as low a concentration of nucleic acid denaturing agents as possible.

Oppositely-charged molecules are able to bind with one another by electrostatic interaction, effectively neutralizing all or part of the charge on one another. Because the hybridization rate enhancement methods described herein are believed to rely, at least in part, on electrostatic attractions between PCAC and nucleic acid molecules, the binding solution should comprise as low a concentration as possible or practical of molecules that are able to bind with and neutralize the charge of either the PCAC or the nucleic acid.

Often, suspensions of nucleic acids that are prepared for hybridization reactions contain one or more of the foregoing agents that can interfere with the hybridization rate enhancement described herein. In such instances, it can be preferable to treat the nucleic acid-containing suspension in such a way as to remove, or reduce the concentration of, those agents prior to performing a hybridization reaction as described herein. Numerous such methods are known in the art, depending on the identity of the agent.

Hybridization rate enhancement effected using the methods described herein is believed to be based, at least in part, on a target nucleic acid-concentrating effect attributable to electrostatic attraction between the PCAC and the target nucleic acid. Once the target nucleic acid has been concentrated in the vicinity of the SNABA, the role of the PCAC can be viewed as accomplished. Excessive interaction between the PCAC and the target nucleic acid can inhibit binding between the target nucleic acid and the SNABA. Furthermore, solution conditions (e.g., low pH) that enhance interaction between the target nucleic acid and the PCAC can be sub-optimal for binding between the target nucleic acid and the SNABA. For this reason, it can be beneficial to alter or replace the binding solution after the target nucleic acid has been attracted to the PCAC on the substrate. Alteration of the binding solution can comprise, for example, adding an agent (e.g., an HCl, NaOH, or buffer solution) that alters the pH of the binding solution, adding an agent that increases the ionic strength of the binding solution, or both. The binding solution can be replaced, for example, by decanting, aspirating, or evaporating the binding solution (i.e., leaving target nucleic acid bound in a salt form with the PCAC on the substrate) and applying a replacement solution in its place. By way of example, when the SNABA is a protein that specifically binds with a certain nucleic acid sequence and the PCAC is a polypeptide comprising numerous histidine residues, lowering the pH of the binding solution (e.g., to pH 4 or 5) can enhance attraction between the PCAC and a nucleic acid in a sample. However, the conformation of the protein can be altered at the lowered pH to the extent that specific binding between the protein and the nucleic acid is inhibited. In this instance, the rate of hybridization can be enhanced by contacting the nucleic acid with a substrate having the PCAC and the protein bound to a region thereon in the presence of a binding solution having the lower pH and thereafter adding an agent to the binding solution that adjusts the pH to a value at which specific binding between the protein and the nucleic acid is less inhibited.

In one aspect, the present invention relates to a device for hybridizing a first nucleic acid (e.g., a nucleic acid target molecule) with a SNABA. The device comprises a substrate having the SNABA and a PCAC bound thereto, the PCAC having the characteristics described herein. As described above, the rate at which the hybridization reaction occurs can be increased (and the corresponding hybridization period can be decreased) by using the device as described herein.

Another aspect of the invention relates to a kit for use in nucleic acid hybridization reactions. The kit comprises the device described herein and an instructional material that describes use of the device for hybridizing the nucleic acid and the SNABA of the device. The kit can further comprise one or more wash or rinse solutions, the binding solution, dyes or other labels for the nucleic acid, and other reagents or apparatus useful for performing the hybridization reaction or for detecting hybridization.

The invention is further described by reference to the following experimental examples. These examples are provided for purposes of illustration only, and the invention is not limited to the specific embodiments disclosed in the examples. Instead, the invention encompasses all variations which are evident as a result of the teaching provided herein.

EXAMPLES

The examples demonstrate that factors such as the size and cationizability of the PCAC, relative concentrations of SNABAs and PCACs at the hybridization region of the substrate (designated co-print ratios in the examples), and length and sequence content of both the nucleic acid and the SNABA affect nucleic acid hybridization rates. Unless otherwise indicated, methods used in the Examples were the same as those described in Zhang et al. (2001, Nucleosides, Nucleotides & Nucleic Acids 20(4–7):1251–1254).

Example 1

Peptide Library Construction and Characterization

Several histidine-containing peptides were evaluated, and the sequences of these peptides are listed in Table 1 using standard single-letter amino acid codes. These peptides differed in size and sequence, and indicated ("$CONH_2$") peptides were amidated by substituting the carboxyl terminal hydroxyl moiety with an amine moiety.

TABLE 1

| Designation | Sequence or Identity | SEQ ID NO: |
|---|---|---|
| P0 | Streptavidin[#] | N/A |
| P1 | HHE | 1 |
| P2 | HHFE | 2 |
| P3 | HFG | 3 |
| P4 | HFEG | 4 |
| P5 | HE(CONH$_2$) | 5 |
| P6 | HFEN(CONH$_2$) | 6 |
| P7 | Histamine | 7 |
| P8 | Histidine | 8 |
| P9 | GKH | 9 |
| P10 | KH(CONH$_2$) | 10 |
| P11 | KH | 11 |
| P12 | KHH(CONH$_2$) | 12 |
| P13 | KHH | 13 |
| P14 | KHHH | 14 |
| P15 | KHHHHK(CONH$_2$) | 15 |
| P17 | KHHHHKHHHHK(CONH$_2$) | 16 |
| P18 | KHHHHKHHHHKHHHHK(CONH$_2$) | 17 |
| P20 | KHKHKHKHKH(CONH$_2$) | 18 |
| P21 | HKH | 19 |
| P22 | HHK | 20 |
| P23 | KHHH(CONH$_2$) | 21 |
| P24 | KHHHH(CONH$_2$) | 22 |

[#]IMMUNOPURE ®, Pierce Chemical Company

Example 2

Binding of a 15-mer Polynucleotide with Histidine-Containing Peptides

Peptides P0 through P14 were arrayed onto an activated NHS(N-hydroxysuccinimide) polyacrylamide thin film substrate and covalently linked using standard NHS ester attachment chemistry (but without using the EDAC capping technique used by Zhang et al.). Each peptide was applied as a 5 nanoliter sample of a 200 micromolar peptide suspension in 150 millimolar sodium bicarbonate buffer (the suspension having a pH of about 9.3) using a BIOCHIP ARRAYER® (Packard BioSciences) spotting device, and each peptide was spotted as five replicates. A fluorescently-labeled 15-mer polynucleotide was contacted, at a concentration of 10 nanomolar, with the thin-film substrate for 15 minutes in the presence of a binding solution that comprised 2 millimolar sodium acetate at pH 4.5. Thereafter, the substrate was washed for 10 minutes by exposing it to a wash solution comprising 2 millimolar sodium acetate at pH 4.5. The peptide array was imaged under fluorescing conditions using a SCAN ARRAYS® MODEL 4000XL imaging device (Packard BioSciences), and the image is shown in FIG. 1A. The map indicating the arrangement of peptides is shown in FIG. 1B.

Comparing primer pairs P8 and P7, P11 and P10, and P13 and P12, it is apparent that the carboxyl terminal amine moiety enhanced binding of the polynucleotide to the peptide, relative to the corresponding non-aminated peptide. Furthermore, the greater the number of positively-charged residues in the peptide, the greater was the binding of the polynucleotide to the peptide (compare series P7, P10, and P12 or series P8, P11, P13, and P14).

The data provided in this example demonstrate that rate of attraction of fluorescently-tagged DNA target molecules can be altered by manipulating parameters such as lysine content, histidine content, and amide capping.

Example 3

Evaluation of Lysine- and Histidine-Containing Peptides on Hydrogel Surface

Figures 2A, 2B:
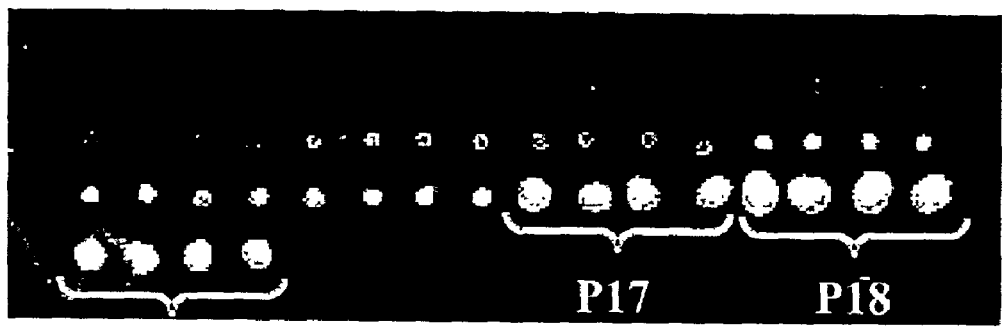
FIG. 2A is a map showing the arrangement of peptides spotted on the array shown in FIG. 2B.
FIG. 2B is an image of a peptide array described in Example 3, under fluorescing conditions.

Peptides P10 through P15, P17, P18, and P20 through P24 were arrayed onto and covalently attached to a polyacrylamide thin-film substrate, in the configuration shown in FIG. 2A. Each peptide was applied as a 3 nanoliter sample of a 50 micromolar peptide solution in 150 millimolar sodium bicarbonate buffer (pH about 9.3) using the BIOCHIP ARRAYER® (Packard BioSciences) spotting device, and each peptide was spotted as four replicates.

A fluorescently-labeled 153-base pair double-stranded amplicon was heat-denatured and then contacted, at a concentration of 10 nanomolar, with the substrate for 15 minutes in the presence of a binding solution that comprised 2 millimolar sodium acetate at pH 4.5. Thereafter, the substrate was washed for 10 minutes by exposing it to a wash solution comprising 2 millimolar sodium acetate at pH 4.5.

The peptide array was imaged under fluorescing conditions, and the image is shown in FIG. 2B. The largest and most positively charged peptides, P17, P18, and P20, exhibited the greatest attraction for the larger double-stranded nucleic acid.

Example 4

Hybridization Studies Using Oligonucleotide/Peptide Co-Prints

SNABA-Target Model System

The model system employed to evaluate the peptide mediated hybridization rate enhancement strategy was derived from the rat neurofibromatosis gene (rNeu), in which a mutation (T→A) at nucleotide residue position 2012 is associated with a breast cancer phenotype. A series of oligonucleotide probes varying in length from 11 to 30 nucleotides was synthesized to span the region of this mutation. Probes were engineered to contain either the wild type sequence or the mutant sequence. Variations of the 20 mer and 30 mer probes containing 10% and 20% mismatched nucleotide residues were synthesized in order to evaluate the specificity with which the probes bound. In addition, synthetic target polynucleotides containing a terminal Cy3 fluorescent modification were constructed.

PCR primers were synthesized for amplifying a 153-residue amplicon from plasmid DNA. That amplicon contained the probe binding site in the middle of the amplified sequence. PCR primers were also designed to contain a terminal Cy3 tag on the strand to be interrogated, and a terminal biotin moiety on the non-interrogating strand to allow single-strand isolation using streptavidin coated magnetic beads.

The nucleotide sequence information for this model system is listed in Tables 2 and 3. Each of the probes listed in Table 2 has a 5' amine modification and each of the targets listed in Table 3 has a 5' Cy3 modification.

TABLE 2

| Probe Name | Nucleotide Sequence | SEQ ID NO: |
|---|---|---|
| 11 | GTAGTGGGCG T | 23 |
| 11m | GTAGAGGGCG T | 24 |
| 13 | CTGTAGTGGG CGT | 25 |
| 13m | CTGTAGAGGG CGT | 26 |
| 15 | AACTGTAGTG GGCGT | 27 |
| 15m | AACTGTAGAG GGCGT | 28 |
| 20 | CAACTGTAGT GGGCGTCCTG | 29 |
| 20m2 | CAACTGTAGA GGGCATCCTG | 30 |
| 20m4 | CAACAGTAGA GTGCATCCTG | 31 |
| 30 | CATTGCAACT GTAGTGGGCG TCCTGCTGTT | 32 |
| 30m3 | CATTGCAACA GTAGAGGGCA TCCTGCTGTT | 33 |
| 30m6 | CATTTCAACA GTAGAGTGCA TCCTTCTGTT | 34 |

TABLE 3

| Target Name | Nueleotide Sequence | SEQ ID NO: |
|---|---|---|
| T15-Cy3 | ACGCCCACTA CAGTT-(CY3) | 35 |
| T30-Cy3 | AACAGCAGGA CGCCCACTAC AGTTGCAATG-(CY3) | 36 |

Evaluation of Oligonucleotide and Peptide Co-Printing Ratios

Because the same (N-hydroxysuccinimidyl-based) coupling chemistry was used to bind polynucleotide SNABAs and polypeptide PCACs to the polyacrylamide substrate, potential displacement of polynucleotide probes by co-printed polypeptides was investigated. To accomplish this, sets of probe-spots (each set including 9 replicates) were printed onto a polyacrylamide thin-film substrate. The fluid that was printed onto the substrate contained a fluorescently labeled polynucleotide probe at a concentration of 25 micromolar. For one set of probe-spots, the fluid contained only the polynucleotide probe. For other sets of probe-spots, the fluid also contained a polypeptide at a concentration corresponding to a selected ratio, relative to the concentration-of the polynucleotide probe. The ratios ranged from 1:1 (25 micromolar polynucleotide probe+25 micromolar polypeptide) to 1:16 (25 micromolar polynucleotide probe+400 micromolar polypeptide).

Figure 3:
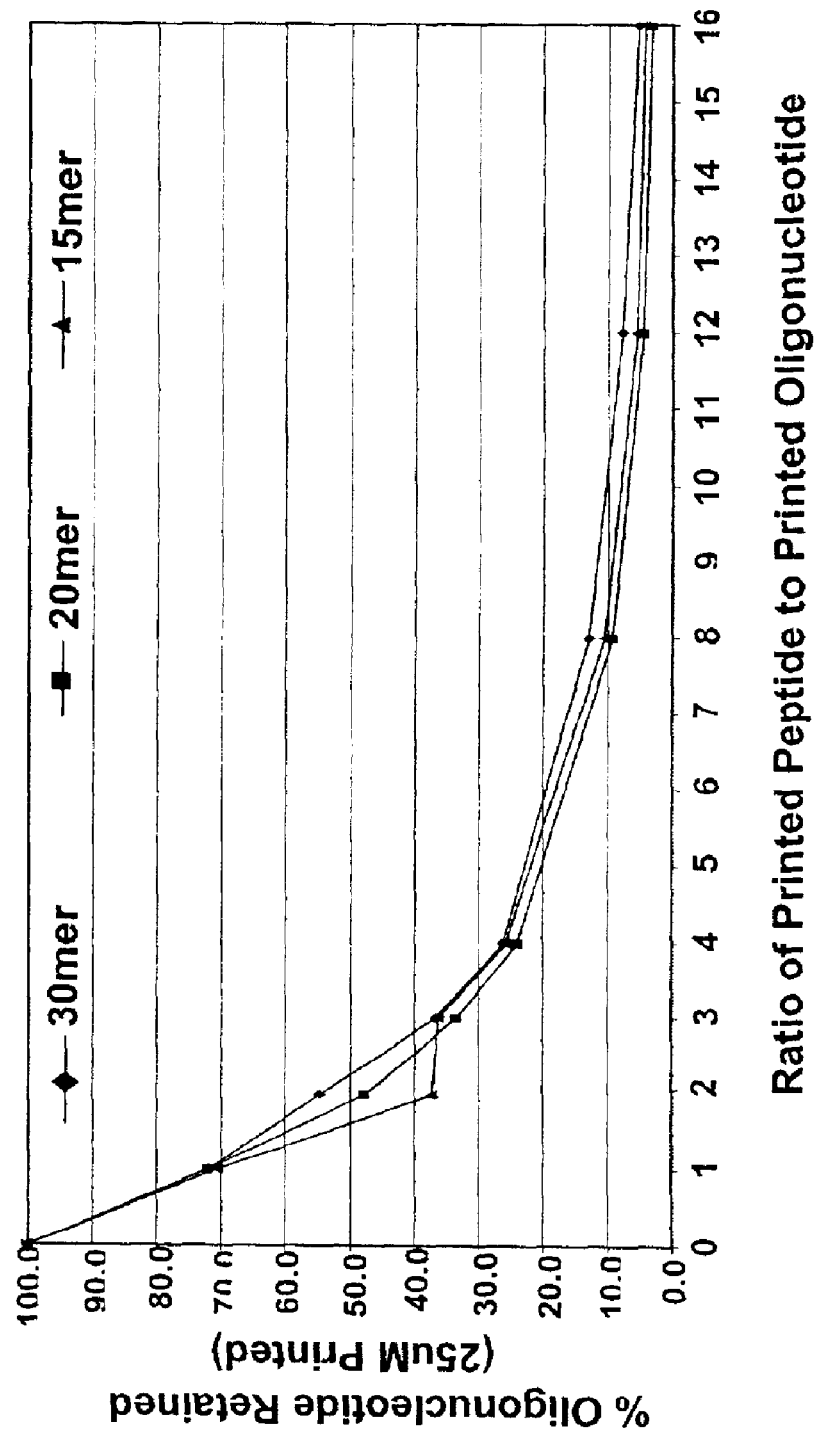
FIG. 3 is a graph that indicates the relationship between the percentage of polynucleotide moieties bound to a hydrogel surface as a function of the polynucleotide/peptide co-print ratio, relative to the amount of polynucleotide moieties bound to the hydrogel substrate in the absence of the peptide.

After printing and washing the probe-spots, a baseline value of 100% was established for the polynucleotide probe printed alone. The diminution of signal, relative to the baseline value, was determined for each of the probe-:polypeptide co-printing ratios. The results of this analysis are shown in FIG. 3. Above about a 1:3 ratio of probe:polypeptide, the polypeptide begins to out-compete the probe for binding sites on the polyacrylamide substrate, with the result that polypeptide binding with the substrate reduces the amount of probe attached to the substrate to a degree that the hybridization signal is significantly adversely affected. Below about a 1:1 ratio of probe:polypeptide, the attractive function of the polypeptide PCAC can be diminished, presumably because so little PCAC is bound that its effect on attracting target nucleic acids to the substrate does not significantly enhance the hybridization signal. For these reasons, probe:polypeptide ratios in the range from 1:1 to 1:3 are preferred, such as a ratio of 1:2 (i.e., roughly twice as many molecules of PCAC in the solution used to modify the substrate as the number of molecules of SNABA). The co-binding ratios corresponding to these co-print ratios were not determined, but could be using standard techniques.

Hybridization of Synthetic Targets on Co-Printed Oligonucleotide/Peptide Arrays

Figure 4:
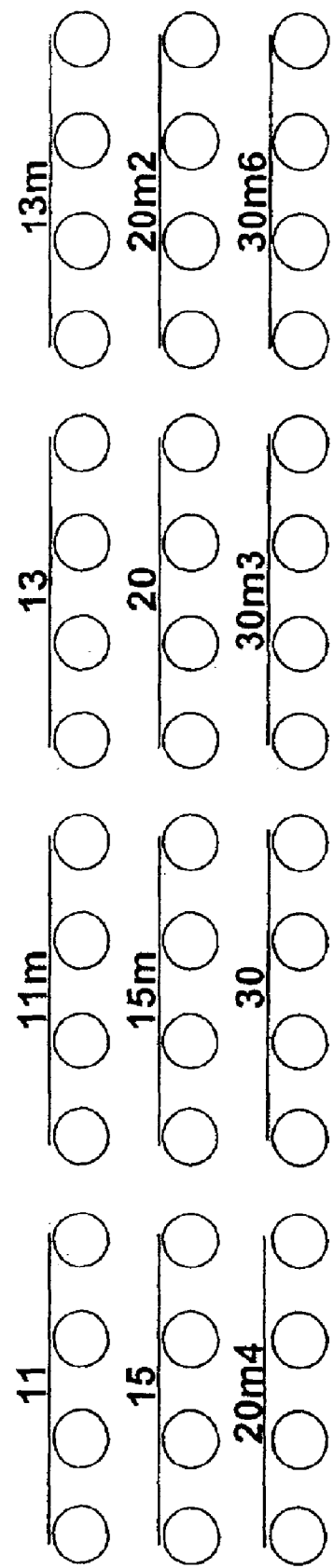
FIG. 4 is a map of the array of oligonucleotide probes used in Example 4 and shown in FIGS. 5, 6, 7, and 8. In the map, the designation atop the four replicates (represented by circles) indicates the probe that was spotted at that location. Probe designations are listed in Table 2. In the probe designation, the numeral indicates the length of the probe in nucleotide residues, "m" indicates occurrence of a single mismatch, "m2" and "m3" indicate occurrence of 10% mismatched residues, and "m4" and "m6" indicate occurrence of 20% mismatched residues.

In order to assess the hybridization competency of co-printed probes and peptides under low pH (4.5) and low cation conditions (2 millimolar Na$^+$), an array was designed to investigate the effects of probe length and mismatch composition. The base microarray map is shown in FIG. 4, in which the designations above the quadruple replicates refers to the probe designation in Table 2. In order to assess the effect of probe:peptide (SNABA:PCAC) ratios, the array was printed with selected ratios ranging from 1:0 (25 micromolar probe+no peptide) to 1:2 (25 micromolar probe+50 micromolar peptide).

Figure 5:
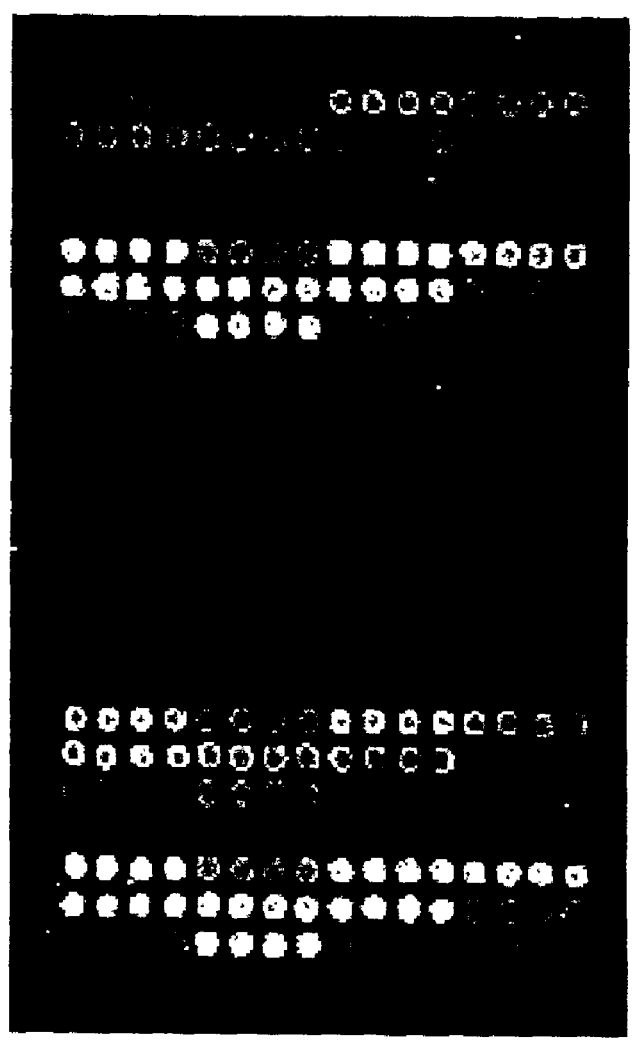
FIG. 5 is an image of a probe array co-printed with peptide P18 at the indicated co-print ratios and hybridized with a Cy3 conjugated 15 mer synthetic target.

FIG. 5 shows the results of an experiment in which the effect of co-printing the peptide P18 at 1:0, 1:1, 1:1.5, and 1:2 probe:peptide ratios was evaluated, using a fluorescently (Cy3) labeled 15-mer target oligonucleotide. These results are an example of attraction and specific duplex formation using a synthetic Cy3 labeled 15-mer target oligonucleotide. In this example, the substrate was contacted with a binding solution comprising 10 nanomolar target oligonucleotide in 2 millimolar sodium acetate at pH 4.5 for 15 minutes, and then washed by contacting the substrate with a wash solution comprising 0.5×SSC at pH 7.5 for 15 minutes. Both the hybridization signal and the match:mismatch discrimination ratio increase dramatically as the probe:P18 co-print ratio increases from 1:0 to 1:2. These results demonstrate that addition of a PCAC to a hybridization region at which a SNABA occurs can increase the rate, degree, and specificity of hybridization of a nucleic acid with the SNABA.

Figure 6A:
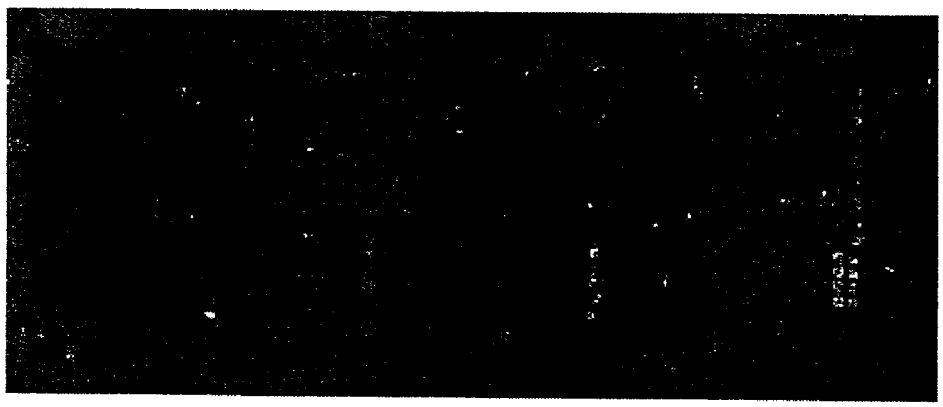
FIG. 6A is an image of a probe array co-printed with peptide P17 and evaluated for attraction properties using double-stranded amplicon target.
Figure 6B:
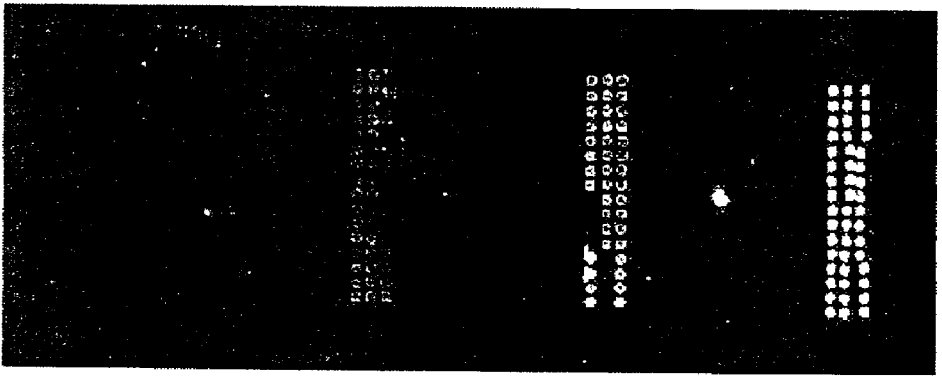
FIG. 6B is an image of a probe array co-printed with peptide P18 and evaluated for attraction properties using double-stranded amplicon target.
Figure 6C:
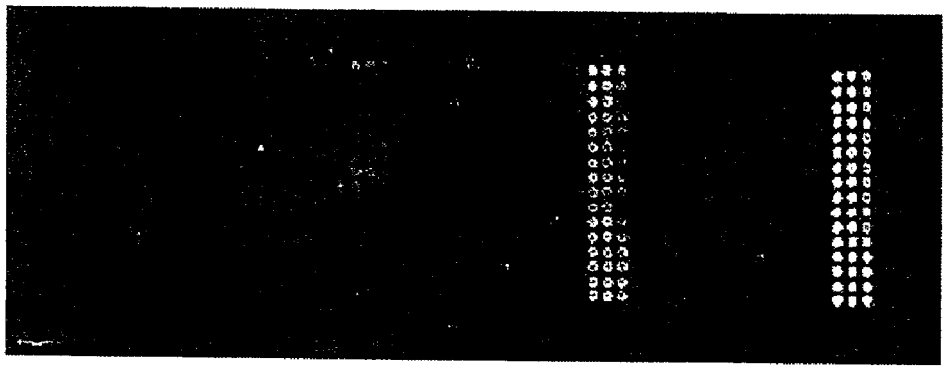
FIG. 6C is an image of a probe array co-printed with peptide P20 and evaluated for attraction properties using double-stranded amplicon target.

Similar experiments were performed by co-printing the probe arrays depicted in FIG. 4 with the peptides P17, P18, and P20 at selected probe:polypeptide ratios. The probe arrays were contacted with a 10 nanomolar suspension of a fluorescently labeled 153 base pair nucleic acid (i.e., the double-stranded rNeu amplicon target) in the presence of a solution comprising 2 millimolar sodium acetate buffer (pH 4.5) for 15 minutes, after which the substrate was rinsed by contacting it for 15 minutes with a second binding solution comprising 2 millimolar sodium acetate buffer (pH 4.5). These results are shown in FIG. 6 (FIG. 6A corresponds to P17; FIG. 6B corresponds to P18; FIG. 6C corresponds to P20) and demonstrate that P18 has the best overall attraction properties for amplicon-sized, double-stranded DNA targets.

Attraction of an amplicon target DNA is greatly reduced, relative to the attraction observed for the shorter synthetic nucleic acids that were tested. Without being bound by any particular theory of operation, the reduced attraction of an amplicon target is believed to occur because the amplicon target is double stranded and only one of the two DNA strands is labeled. The reduction in attraction signal likely results from competition by the non-labeled DNA strand for the peptide charge-based attraction. The non-labeled DNA strand can also interfere with hybridization to the printed probes since it is in such close proximity to and a perfect complement to the target strand to be interrogated. Thus when the low-salt induction solution is replaced with the high-salt binding solution, re-annealing of the double stranded amplicon is believed to be as likely or more likely to occur than hybridization of the target strand to the probe. These data suggest that it can be preferable, where possible, to hybridize single-stranded (rather than double-stranded) nucleic acids with a SNABA in the presence of a PCAC, at least when the SNABA is an oligonucleotide (or when an array of oligonucleotides is used).

Figure 7:
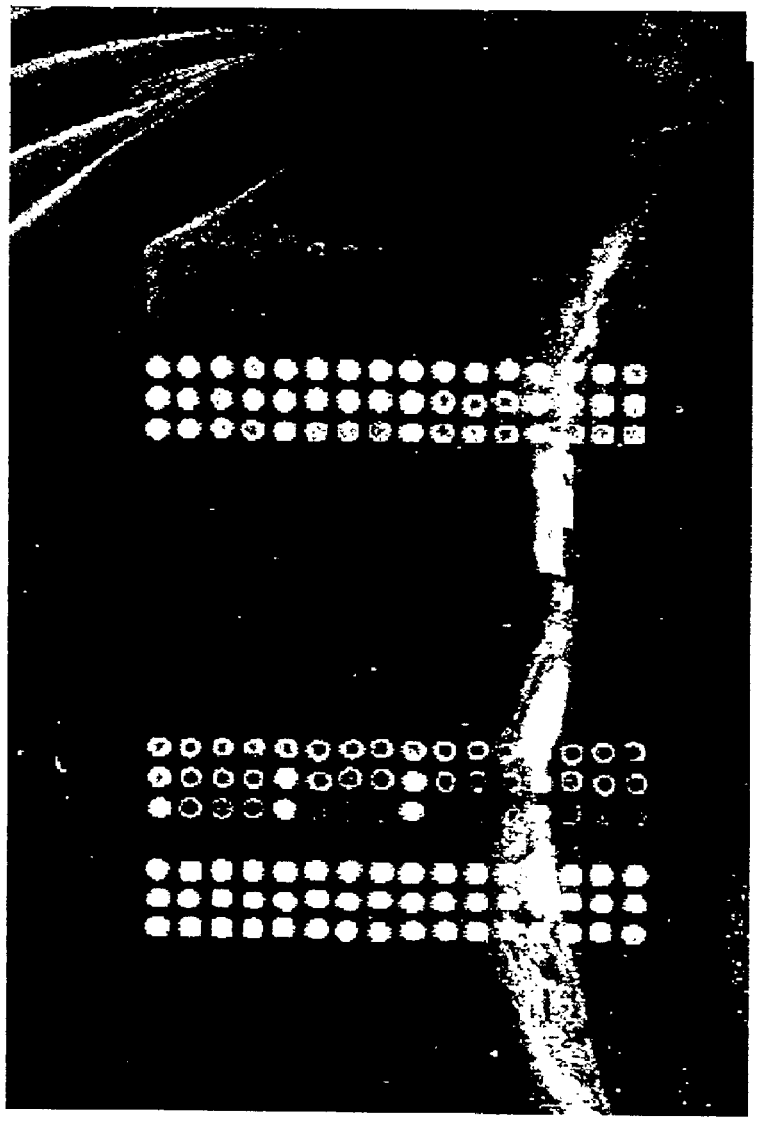
FIG. 7 is an image of a probe array co-printed with peptide P18 and evaluated for attraction properties using a single-stranded amplicon target.

When double-stranded nucleic acids are made, it is often possible to selectively tag one of the two strands, such that that strand can be recovered or extracted from the sample prior to contacting the sample with the SNABA- and PCAC-bound hybridization substrate. For example, one strand of an amplicon target can be tagged with a biotin molecule, and streptavidin-coated magnetic beads can be used to separate the biotinylated strand from the non-biotinylated strand. Either strand can then be contacted with the hybridization substrate. An experiment was performed in order to demonstrate this effect. A 10 nanomolar suspension of a single-stranded amplicon target nucleic acid was contacted with a co-printed rNeu probe:P18 peptide array prepared as described herein. The amplicon nucleic acid and the array were contacted for 15 minutes in 2 millimolar sodium acetate at pH 4.5, and then rinsed by contacting the substrate with a second binding solution comprising 2 millimolar sodium acetate buffer (pH 4.5) for 15 minutes. Comparing FIGS. 6B and 7, it is observed that greater attraction of the fluorescently labeled, single-stranded nucleic acid to the substrate occurred than did attraction of the labeled, double-stranded nucleic acid.

Figure 8:
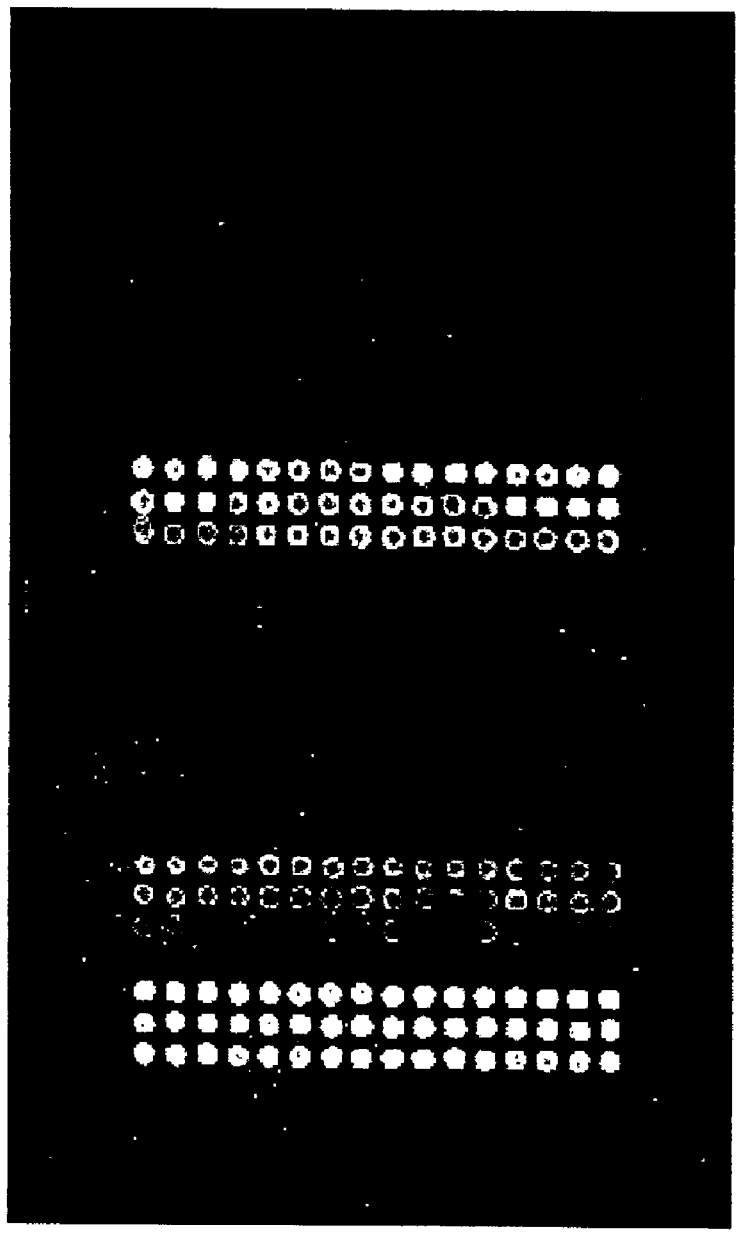
FIG. 8 is an image of a probe array co-printed with peptide P18 and evaluated for hybridization properties using a single-stranded amplicon target.

FIG. 8 demonstrates a prototype experiment that utilizes the HRE strategy. In this experiment, a probe array that is co-printed with P18 is contacted for 15 minutes with a binding solution comprising 10 nanomolar labeled, single-stranded amplicon polynucleotide and 50 millimolar sodium acetate at pH 4.5. Next, the array was treated for 15 minutes by contacting the array with a second binding solution comprising 0.5×SSC at pH 7.5. The resulting hybridization signal increased as the co-print ratio increased from 1:0 to 1:2. The match:mismatch discrimination ratio is roughly 2:1 when comparing the 20-mer and 30-mer perfect match probes (probes 20 and 30) to their corresponding 20% mismatch probes (20m4 and 30m6, respectively). These results indicate that the HRE methods described herein can be used to enhance the rate, degree, and specificity of hybridization of a nucleic acid in a sample with a SNABA bound to a substrate in the presence of a PCAC.

The disclosure of every patent, patent application, and publication cited herein is incorporated herein by reference in its entirety.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of hybridizing a nucleic acid and a specific nucleic acid-binding agent (SNABA), the method comprising contacting, in the presence of a binding solution,
   i) the nucleic acid and
   ii) a substrate having a hybridization region, wherein the SNABA and a polycationizable attractor compound (PCAC) are bound to the substrate in the hybridization region, and wherein the PCAC comprises at least two different moieties that are positively charged at the pH of the binding solution, including at least one cationizable moiety having a pK value in the pH range 4 to 9.5,
whereby the nucleic acid hybridizes with the SNABA.

2. The method of claim 1, wherein the substrate has a background region to which neither the SNABA nor the PCAC is bound.

3. The method of claim 2, wherein the hybridization and background regions are adjacent.

4. The method of claim 2, wherein the substrate has a first control region to which the SNABA is bound and to which the PCAC is not bound.

5. The method of claim 2, wherein the substrate has a second control region to which the PCAC is bound and to which the SNABA is not bound.

6. The method of claim 1, wherein both the SNABA and the PCAC are covalently bound to the substrate in the hybridization region.

7. The method of claim 6, wherein the PCAC is covalently bound to the substrate near a linear end of the PCAC.

8. The method of claim 6, wherein the molar amount of the SNABA bound to the hybridization region is about equal to the molar amount of the PCAC bound to the hybridization region.

9. The method of claim 6, wherein the molar amount of the PCAC bound to the hybridization region is not more than about three times the molar amount of the SNABA bound to the hybridization region.

10. The method of claim 1, wherein the PCAC comprises at least five moieties that are positively charged at the pH of the binding solution.

11. The method of claim 10, wherein the PCAC comprises at least ten moieties that are positively charged at the pH of the binding solution.

12. The method of claim 11, wherein the PCAC comprises at least fifteen moieties that are positively charged at the pH of the binding solution.

13. The method of claim 1, wherein the PCAC does not comprise a moiety that is negatively charged at the pH of the binding solution.

14. The method of claim 1, wherein the PCAC is a polypeptide that comprises not more than 25 amino acid residues.

15. The method of claim 14, wherein the polypeptide comprises from 5 to about 20 amino acid residues.

16. The method of claim 15, wherein the polypeptide comprises from 10 to 20 amino acid residues.

17. The method of claim 14, wherein the carboxyl terminus of the polypeptide is amidated.

18. The method of claim 14, wherein the polypeptide comprises at least one histidine residue.

19. The method of claim 18, wherein the polypeptide comprises at least one lysine residue.

20. The method of claim 14, wherein the polypeptide comprises a region having the amino acid sequence of one of SEQ ID NOs: 1, 2, and 9–22.

21. The method of claim 20, wherein the polypeptide has the amino acid sequence of one of SEQ ID NOs: 1, 2, and 9–22.

22. The method of claim 14, wherein the polypeptide comprises a region having the amino acid sequence of one of SEQ ID NOs: 16–18.

23. The method of claim 22, wherein the polypeptide has the amino acid sequence of one of SEQ ID NOs: 16–18.

24. The method of claim 1, wherein the substrate-bound PCAC has the chemical structure $$\text{Su-Lk-X-(Lys-His}_n)_m\text{-X-Z}$$

wherein
   Su is the substrate;
   Lk is a linker;
   each X is independently 0 to 25 amino acid residues;
   n is 1 to 5;
   m is 1 to 10; and
   Z is one of a hydrogen radical, a carboxylate capping moiety, and the SNABA.

25. The method of claim 24, wherein the linker is selected from the group consisting of a covalent bond and an N-hydroxysuccinimidyl moiety.

26. The method of claim 24, wherein each X is independently 0 to 25 amino acid residues having side chains that are not negatively charged at the pH of the binding solution.

27. The method of claim 24, wherein each X is independently 0 to 25 amino acid residues, and wherein any side chain carboxylate moiety of these residues is capped.

28. The method of claim 24, wherein Z is either a hydrogen radical or an amide moiety.

29. The method of claim 28, wherein Z is an amide moiety having the chemical structure —NR$^1$R$^2$, wherein each R$^1$ and R$^2$ is independently selected from the group consisting of a hydrogen radical and C$_1$–C$_6$ straight chain alkyl radicals, optionally substituted with one or more hydroxyl or amine moieties.

30. The method of claim 28, wherein Z is a cyclic amide moiety having the chemical structure —NR$^3$R$^4$, wherein R$^3$ and R$^4$ are together a C$_5$–C$_8$ dialkylene moiety, optionally substituted with one or more hydroxyl or amine moieties.

31. The method of claim 24, wherein Z is —NH$_2$.

32. The method of claim 1, wherein the substrate-bound compound has the chemical structure

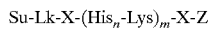

Su-Lk-X-(His$_n$-Lys)$_m$-X-Z wherein

Su is the substrate;

Lk is a linker;

each X is independently 0 to 25 amino acid residues;

n is 1 to 5;

m is 1 to 10; a and

Z is one of a hydrogen radical, a carboxylate capping moiety, and the SNABA.

33. The method of claim 1, wherein the SNABA is a polynucleotide.

34. The method of claim 33, wherein the polynucleotide is complementary to the nucleic acid.

35. The method of claim 1, wherein the SNABA is selected from the group consisting of a polynucleotide analog, a sequence-specific nucleic acid-binding protein, a structure-specific nucleic acid-binding protein, and a conformation-specific nucleic acid-binding protein.

36. The method of claim 1, wherein the SNABA and the PCAC are conjugated.

37. The method of claim 1, wherein the hybridization region is a portion of a substantially flat surface of the substrate.

38. The method of claim 1, wherein the substrate is substantially impermeable to the binding solution.

39. The method of claim 38, wherein the substrate is selected from the group consisting of glasses, silicon substrates, and plastics.

40. The method of claim 1, wherein the substrate is porous.

41. The method of claim 1, further comprising contacting the substrate with a second binding solution after contacting the substrate with the binding solution, wherein the pH of the second binding solution is greater than the pH of the binding solution.

42. The method of claim 41, wherein the binding solution is removed and replaced by the second binding solution.

43. The method of claim 41, wherein a pH modifying agent is added to the binding solution to yield the second binding solution.

44. The method of claim 43, wherein the net charge of the PCAC is less positive in the presence of the second binding solution than in the presence of the binding solution.

45. The method of claim 44, wherein the net positive charge of the PCAC in the presence of the second binding solution is not more than half the net positive charge of the PCAC in the presence of the binding solution.

46. The method of claim 44, wherein the net positive charge of the PCAC in the presence of the second binding solution is not more than one-fourth the net positive charge of the PCAC in the presence of the binding solution.

47. The method of claim 43, wherein the ionic strength of the second binding solution is greater than the ionic strength of the binding solution.

48. The method of claim 43, wherein the substrate is rinsed with a stream of the second binding solution.

49. The method of claim 43, further comprising contacting the substrate with a first rinse solution after contacting the substrate with the second binding solution, wherein the first rinse solution has a different temperature than the second binding solution.

50. The method of claim 49, wherein the temperature of the first rinse solution is higher than the temperature of the second binding solution.

51. The method of claim 1, wherein the molecular weight of the PCAC is not greater than about 15000.

52. A device for hybridizing a nucleic acid and a specific nucleic acid-binding agent (SNABA) in the presence of a binding solution, the device comprising a substrate having a hybridization region, wherein the hybridization region has bound thereto:

i) the SNABA and ii) a polycationizable attractor compound (PCAC), wherein the PCAC comprises at least two different moieties that are positively charged at the pH of the binding solution, including at least one cationizable moiety having a pK value in the pH range 4 to 9.5.

53. The device of claim 52, having the nucleic acid hybridized with the SNABA.

54. A kit for hybridizing a nucleic acid and a SNABA, the kit comprising the device of claim 52 and an instructional material that describes using the device to hybridize the nucleic acid and the SNABA.

55. In a method of hybridizing a nucleic acid and a specific nucleic acid-binding agent (SNABA) by contacting, in the presence of a binding solution, i) the nucleic acid and ii) a substrate having a hybridization region with the SNABA bound thereto, the improvement comprising binding a polycationizable attractor compound (PCAC) with the hybridization region prior to contacting the substrate and the nucleic acid, wherein the PCAC comprises at least two different moieties that are positively charged at the pH of the binding solution, including at least one cationizable moiety having a pK value in the pH range 4 to 9.5, whereby the PCAC improves the rate of hybridization of the nucleic acid and the SNABA.

* * * * *